(12) United States Patent
Kibbe et al.

(10) Patent No.: US 10,738,294 B2
(45) Date of Patent: Aug. 11, 2020

(54) TISSUE FACTOR (TF)—TARGETED NANOTHERAPY

(71) Applicant: Northwestern University, Evanston, IL (US)

(72) Inventors: Melina R. Kibbe, Chicago, IL (US); Samuel I. Stupp, Chicago, IL (US)

(*) Notice: Subject to any disclaimer, the term of this patent is extended or adjusted under 35 U.S.C. 154(b) by 64 days.

(21) Appl. No.: 15/715,977

(22) Filed: Sep. 26, 2017

(65) Prior Publication Data

US 2018/0087039 A1 Mar. 29, 2018

Related U.S. Application Data

(60) Provisional application No. 62/399,773, filed on Sep. 26, 2016.

(51) Int. Cl.
| | |
|---|---|
| *C12N 9/64* | (2006.01) |
| *A61K 47/64* | (2017.01) |
| *A61K 45/06* | (2006.01) |
| *A61K 9/00* | (2006.01) |
| *A61K 38/48* | (2006.01) |
| *A61K 9/70* | (2006.01) |
| *A61K 47/54* | (2017.01) |
| *A61K 47/69* | (2017.01) |

(52) U.S. Cl.
CPC .......... *C12N 9/6437* (2013.01); *A61K 9/0019* (2013.01); *A61K 9/70* (2013.01); *A61K 38/4833* (2013.01); *A61K 45/06* (2013.01); *A61K 47/542* (2017.08); *A61K 47/64* (2017.08); *A61K 47/69* (2017.08); *C12Y 304/21005* (2013.01); *C12Y 304/21006* (2013.01); *C12Y 304/21021* (2013.01)

(58) Field of Classification Search
None
See application file for complete search history.

(56) References Cited

U.S. PATENT DOCUMENTS

| | | |
|---|---|---|
| 6,890,654 B2 | 5/2005 | Stupp et al. |
| 7,371,719 B2 | 5/2008 | Stupp et al. |
| 7,390,526 B2 | 6/2008 | Stupp et al. |
| 7,452,679 B2 | 11/2008 | Stupp et al. |
| 7,491,690 B2 | 2/2009 | Stupp et al. |
| 7,534,761 B1 | 5/2009 | Stupp et al. |
| 7,544,661 B2 | 6/2009 | Stupp et al. |
| 7,554,021 B2 | 6/2009 | Stupp et al. |
| 7,683,025 B2 | 3/2010 | Stupp et al. |
| 7,745,708 B2 | 6/2010 | Stupp et al. |
| 7,838,491 B2 | 11/2010 | Stupp et al. |
| 7,851,445 B2 | 12/2010 | Stupp et al. |
| 8,063,014 B2 | 11/2011 | Stupp et al. |
| 8,080,262 B2 | 12/2011 | Lee et al. |
| 8,114,834 B2 | 2/2012 | Hsu et al. |
| 8,114,835 B2 | 2/2012 | Mata et al. |
| 8,124,583 B2 | 2/2012 | Stupp et al. |
| 8,138,140 B2 | 3/2012 | Stupp et al. |
| 8,450,271 B2 | 5/2013 | Shah et al. |
| 8,512,693 B2 | 8/2013 | Capito et al. |

OTHER PUBLICATIONS

Morgan et al. ("Tissue-Factor Targeted Peptide Amphiphile Nanofibers as an Injectable Therapy to Control Hemorrhage," ACS Nano 2016, 10, 899-909) (Year: 2016).*
Bahnson et al., Targeted Nitric Oxide Delivery by Supramolecular Nanofibers for the Prevention of Restenosis After Arterial Injury, Antioxid Redox Signal, vol. 24(8), pp. 401-418, 2016.
Bertram et al., Intravenous Hemostat: Nanotechnology to Halt Bleeding, Sci Trans Med, vol. 1(11), pp. 11ra22, 2010.
Chan et al., A Synthetic Fibrin-Crosslinking Polymer for Modulating Clot Properties and Inducing Hemostasis, Sci Trans! Med, vol. (277), pp. 277ra39, 2015.
Cui et al., Self-Assembly of Peptide Amphiphiles: From Molecules to Nanostructures to Biomaterials, Biopolymers, vol. 94(1), pp. 1-18, 2010.
Dickinson et al., Identification of surface residues mediating tissue factor binding and catalytic function of the serine protease factor VIIa, PNAS, vol. 93(25), pp. 14379-14384, 1996.
Eastridge et al., Died of Wounds on the Battlefield: Causation and Implications for Improving Combat Casualty Care, J Trauma, vol. 71(1), pp. S4-S8, 2011.
Hartgerink et al., Peptide-amphiphile nanofibers: A versatile scaffold for the preparation of self assembling materials, PNAS, vol. 99(8), pp. 5133-5138, 2002.
Hauser et al., Results of the CONTROL Trial: Efficacy and Safety of Recombinant Activated Factor VII in the Management of Refractory Traumatic Hemorrhage, J Trauma Acute Care Surg, vol. 69(3), pp. 489-500, 2010.
Lashof-Sullivan et al., Intravenously administered nanoparticles increase survival following blast trauma, PNAS, vol. 111, pp. 10293-10298, 2014.
Mayo et al., A recipe for designing water-soluble, β-sheet-forming peptides, Protein Science, vol. 5(7), pp. 1301-1315, 1996.
Morgan et al., Development and Validation of 4 Different Rat Models of Uncontrolled Hemorrhage, JAMA Surg, 150(4), pp. 316-324, 2015.
Morrison et al., Noncompressible Torso Hemorrhage a Review with Contemporary Definitions and Management Strategies, Surg Clin North Am, vol. 92(4), pp. 843-858, 2012.
Moyer et al., Shape Dependent Targeting of Injured Blood Vessels by Peptide Amphiphile Supramolecular Nanostructures, Small, vol. 11(23), pp. 2750-2755, 2015.
Neufeld et al., Safety update on the use of recombinant activated factor VII in approved indications, Blood Reviews, vol. 29, pp. S34-S41, 2015.

(Continued)

*Primary Examiner* — Christina Bradley
(74) *Attorney, Agent, or Firm* — Casimir Jones SC; David W. Staple

(57) ABSTRACT

Provided herein are tissue factor (TF)-targeted nanofibers and methods of treating hemorrhage in a subject therewith. In particular, peptide amphiphiles (PAs) are provided that comprise a TF-targeting peptide sequence and self-assemble under aqueous conditions into PA nanofibers displaying the TF-targeting sequence on the exterior of the nanofiber.

18 Claims, 13 Drawing Sheets

Specification includes a Sequence Listing.

(56) References Cited

OTHER PUBLICATIONS

Perez et al., The Powerful Functions of Peptide-Based Bioactive Matrices for Regenerative Medicine, Ann Biomed Eng, vol. 43(3), pp. 501-514, 2015.
Shoffstall et al., Intravenous Hemostatic Nanoparticles Increase Survival Following Blunt Trauma Injury, Biomacromolecules, vol. 13(11), pp. 3859-3857, 2012.
Shoffstall et al., Tuning Ligand Density on Intravenous Hemostatic Nanoparticles Dramatically Increases Survival Following Blunt Trauma, Biomacromolecules, vol. 14(8), pp. 2790-2797, 2013.
Stannard et al., The epidemiology of noncompressible torso hemorrhage in the wars in Iraq and Afghanistan, J Trauma Acute Care Surg, vol. 74(3), pp. 830-834, 2013.
Toft et al., Co-Assembled Cytotoxic and Pegylated Peptide Amphiphiles Form Filamentous Nanostructures with Potent Anti-Tumor Activity in Models of Breast Cancer, ACS Nano, vol. 6(9), pp. 7956-7965, 2012.
Webber et al., Supramolecular Nanofibers of Peptide Amphiphiles for Medicine, ISR J Chem, vol. 53(8), pp. 530-554, 2013.

* cited by examiner

FIG. 3A
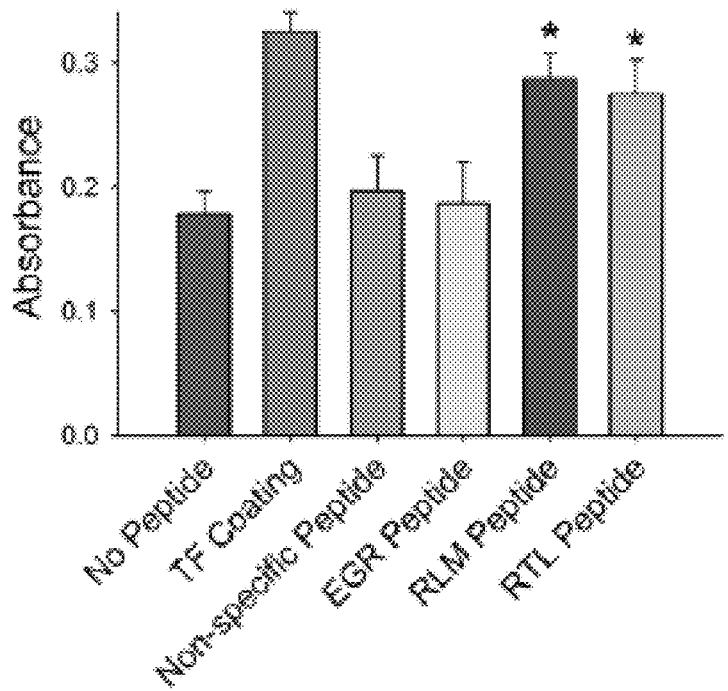
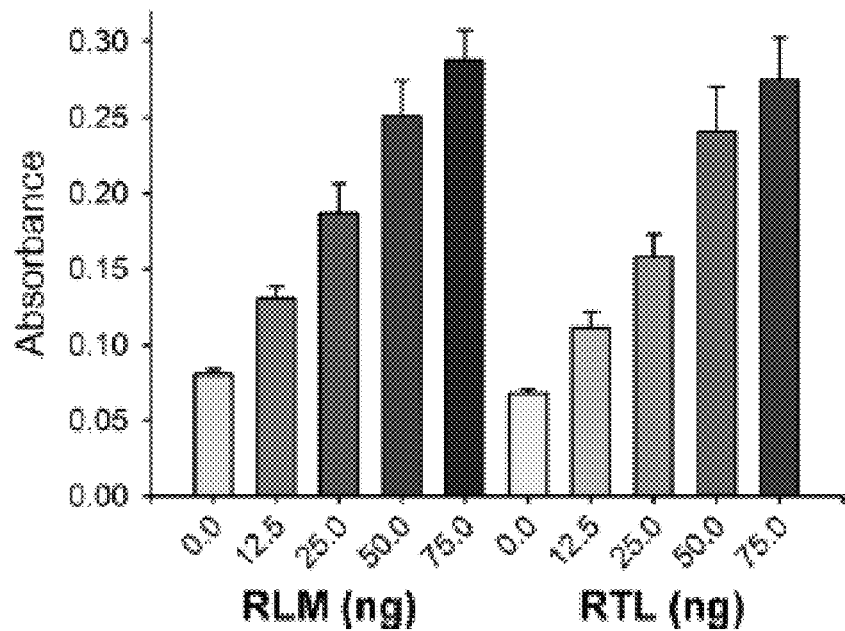
FIG. 3B

FIG. 4B
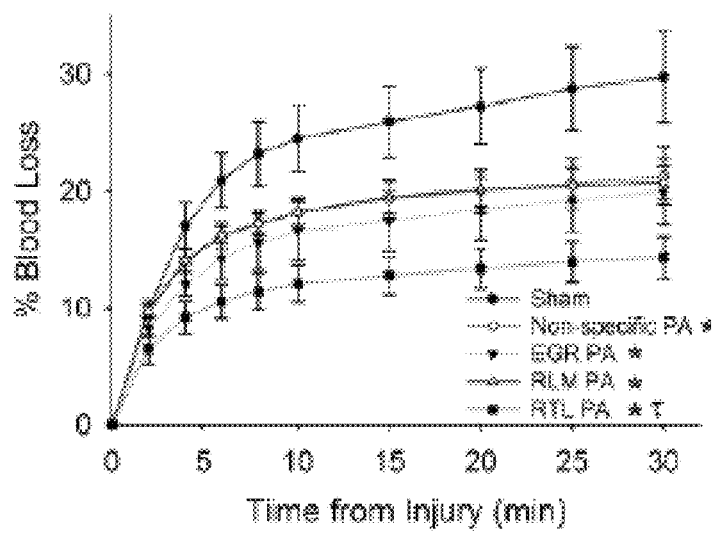
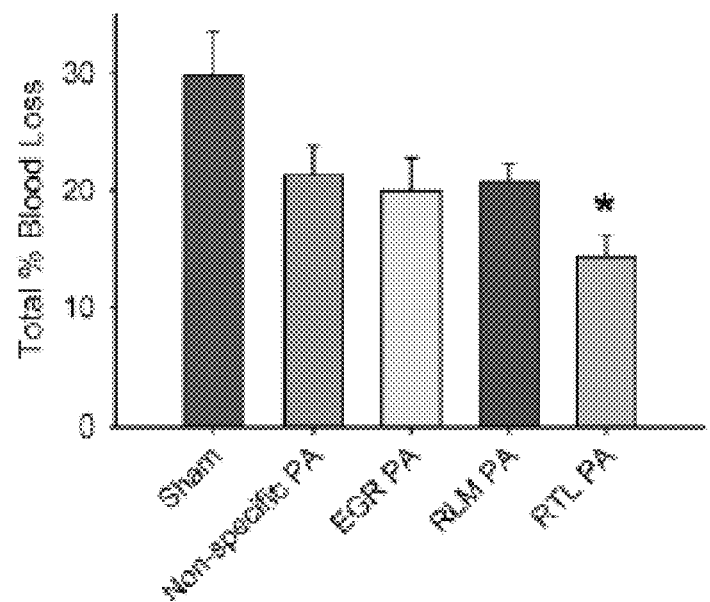
FIG. 4C

FIG. 9A-D
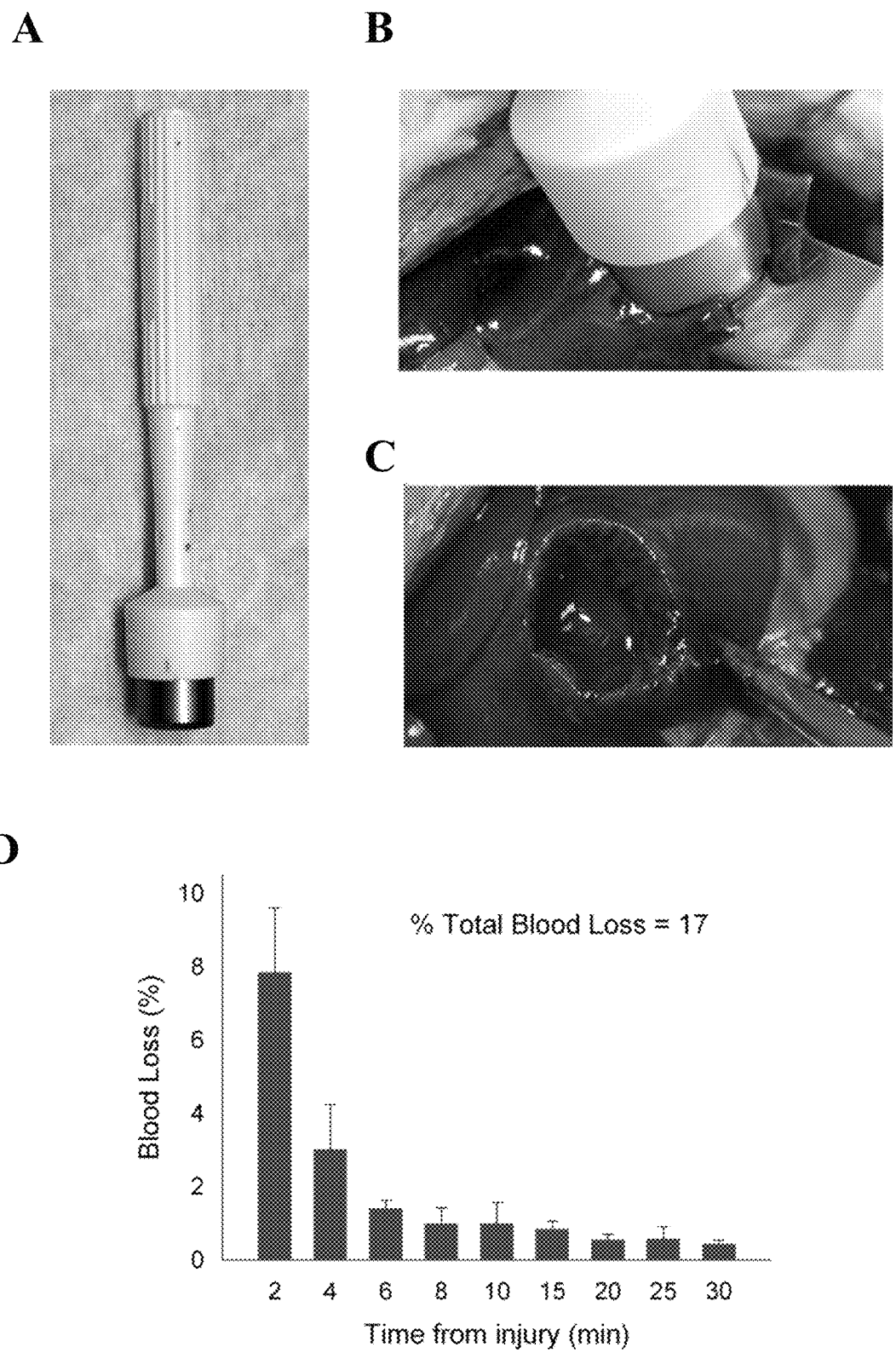

SEQUENCE LISTING

<160> NUMBER OF SEQ ID NOS: 11

<210> SEQ ID NO 1
<211> LENGTH: 13
<212> TYPE: PRT
<213> ORGANISM: Artificial sequence
<220> FEATURE:
<223> OTHER INFORMATION: Synthetic peptide

<400> SEQUENCE: 1

Glu Gly Arg Asn Cys Glu Thr His Lys Asp Asp Gln Leu
1               5                   10

```
<210> SEQ ID NO 2
<211> LENGTH: 13
<212> TYPE: PRT
<213> ORGANISM: Artificial sequence
<220> FEATURE:
<223> OTHER INFORMATION: Synthetic peptide

<400> SEQUENCE: 2

Arg Leu Met Thr Gln Asp Cys Leu Gln Gln Arg Ser Lys
1               5                   10

<210> SEQ ID NO 3
<211> LENGTH: 9
<212> TYPE: PRT
<213> ORGANISM: Artificial sequence
<220> FEATURE:
<223> OTHER INFORMATION: Synthetic peptide

<400> SEQUENCE: 3

Arg Thr Leu Ala Phe Val Arg Phe Lys
1               5

<210> SEQ ID NO 4
<211> LENGTH: 4
<212> TYPE: PRT
<213> ORGANISM: Artificial sequence
<220> FEATURE:
<223> OTHER INFORMATION: Synthetic peptide

<400> SEQUENCE: 4

Val Val Ala Ala
1

<210> SEQ ID NO 5
<211> LENGTH: 7
<212> TYPE: PRT
<213> ORGANISM: Artificial sequence
<220> FEATURE:
<223> OTHER INFORMATION: Synthetic peptide

<400> SEQUENCE: 5

Lys Lys Ala Ala Val Val Lys
1               5

<210> SEQ ID NO 6
<211> LENGTH: 4
<212> TYPE: PRT
<213> ORGANISM: Artificial sequence
<220> FEATURE:
<223> OTHER INFORMATION: Synthetic peptide

<400> SEQUENCE: 6

Ala Ala Val Val
1

<210> SEQ ID NO 7
<211> LENGTH: 6
<212> TYPE: PRT
<213> ORGANISM: Artificial sequence
<220> FEATURE:
<223> OTHER INFORMATION: Synthetic peptide

<400> SEQUENCE: 7

Ala Ala Ala Val Val Val
1               5
```

```
<210> SEQ ID NO 8
<211> LENGTH: 20
<212> TYPE: PRT
<213> ORGANISM: Artificial sequence
<220> FEATURE:
<223> OTHER INFORMATION: Synthetic peptide

<400> SEQUENCE: 8

Glu Gly Arg Asn Cys Glu Thr His Lys Asp Asp Gln Leu Lys Lys Ala
1               5                   10                  15

Ala Val Val Lys
            20

<210> SEQ ID NO 9
<211> LENGTH: 20
<212> TYPE: PRT
<213> ORGANISM: Artificial sequence
<220> FEATURE:
<223> OTHER INFORMATION: Synthetic peptide

<400> SEQUENCE: 9

Arg Leu Met Thr Gln Asp Cys Leu Gln Gln Arg Ser Lys Lys Lys Ala
1               5                   10                  15

Ala Val Val Lys
            20

<210> SEQ ID NO 10
<211> LENGTH: 15
<212> TYPE: PRT
<213> ORGANISM: Artificial sequence
<220> FEATURE:
<223> OTHER INFORMATION: Synthetic peptide

<400> SEQUENCE: 10

Arg Thr Leu Ala Phe Val Arg Phe Lys Lys Lys Ala Ala Val Val
1               5                   10                  15

<210> SEQ ID NO 11
<211> LENGTH: 8
<212> TYPE: PRT
<213> ORGANISM: Artificial sequence
<220> FEATURE:
<223> OTHER INFORMATION: Synthetic peptide

<400> SEQUENCE: 11

Cys Lys Lys Ala Ala Val Val Lys
1               5
```

TISSUE FACTOR (TF)—TARGETED NANOTHERAPY

CROSS-REFERENCE TO RELATED APPLICATIONS

The present invention claims priority benefit from U.S. Provisional Patent Application No. 62/399,773, filed Sep. 26, 2016, which is incorporated by reference in its entirety.

FIELD

Provided herein are tissue factor (TF)-targeted nanofibers and methods of treating hemorrhage in a subject therewith. In particular, peptide amphiphiles (PAs) are provided that comprise a TF-targeting peptide sequence and self-assemble under aqueous conditions into PA nanofibers displaying the TF-targeting sequence on the exterior of the nanofiber.

BACKGROUND

Hemorrhage is the leading cause of mortality in battlefield trauma, and the second leading cause of death in civilian trauma (refs. 1-2; herein incorporated by reference in their entireties) Although therapies have been developed for compressible hemorrhage, non-compressible torso hemorrhage, or bleeding that cannot be controlled by external compression, is a major problem in trauma. Non-compressible torso hemorrhage is defined as a pulmonary injury, a grade IV or greater injury to a solid organ, injury to a named axial vessel, or a pelvic fracture with ring disruption (ref. 3; herein incorporated by reference in its entirety). These are common injuries, representing 13% of all battlefield injuries in Iraq and Afghanistan, with 18% of those injured presenting in shock and requiring immediate control of hemorrhage (ref 4; herein incorporated by reference in its entirety). Current options for non-compressible torso hemorrhage in the far-forward setting are limited. Blood products such as fresh frozen plasma, platelets, and cryoprecipitate can improve coagulopathy (ref. 5; herein incorporated by reference in its entirety), but these products are not readily available in the field due to limited shelf life and stringent storage requirements. While other therapies, such as recombinant Factor VIIa (i.e., Novoseven), have been shown to reduce the need for blood products in trauma patients (ref 6; herein incorporated by reference in its entirety), outcomes with respect to adverse events and mortality are less clear (ref. 7; herein incorporated by reference in its entirety). In addition to the high cost of recombinant Factor VIIa, the original formulation must be stored at 2-8° C., and the newer formulation may only be stored at 25° C. for 6 hours, neither of which is compatible with the battlefield setting (ref. 8; herein incorporated by reference in its entirety). Thus, there is a great need for the development of a therapeutic that can stop non-compressible hemorrhage.

SUMMARY

Provided herein are tissue factor (TF)-targeted nanofibers and methods of treating hemorrhage in a subject therewith. In particular, peptide amphiphiles (PAs) are provided that comprise a TF-targeting peptide sequence and self-assemble under aqueous conditions into PA nanofibers displaying the TF-targeting sequence on the exterior of the nanofiber.

In some embodiments, provided herein are compositions comprising tissue factor (TF)-targeted peptide amphiphiles. In some embodiments, the peptide amphiphiles comprise a hydrophobic non-peptide tail, a structured peptide segment, a charged peptide segment, and a TF-targeted peptide. In some embodiments, the hydrophobic non-peptide tail comprises an 8-24 carbon alkyl chain ($C_{8-24}$). In some embodiments, the peptide amphiphile comprises a K residue, and wherein the hydrophobic non-peptide tail is attached to the sidechain of the K residue. In some embodiments, the structured peptide segment comprises VVAA (SEQ ID NO: 4) or any suitable combination or V and/or A residues. In some embodiments, the structured peptide segment has propensity to form β-sheet-like structures or other stabilizing interactions (e.g., that promote self-assembly of adjacent nanofibers) with adjacent structured peptide segments. In some embodiments, the charged peptide segment comprises an acidic, basic, or zwitterionic peptide segment. In some embodiments, the charged peptide segment comprises EE or KK. In some embodiments, the peptide amphiphile comprises KKAAVV(K)-$C_{8-24}$ (SEQ ID NO: 5). In some embodiments, the TF-targeted peptide comprises at least 70% (e.g., 70%, 75%, 80%, 85%, 90%, 95%, 100%) sequence similarity with one of SEQ ID NO: 1, SEQ ID NO: 2, or SEQ ID NO: 3. In some embodiments, the TF-targeted peptide comprises at least 70% (e.g., 70%, 75%, 80%, 85%, 90%, 95%, 100%) sequence identity with one of SEQ ID NO: 1, SEQ ID NO: 2, or SEQ ID NO: 3. In some embodiments, the TF-targeted peptide comprises one of SEQ ID NO: 1, SEQ ID NO: 2, or SEQ ID NO: 3. In some embodiments, the peptide amphiphile comprises EGRNCETHKDDQLKKAAVV(K)-$C_{8-24}$ (SEQ ID NO: 8). In some embodiments, the peptide amphiphile comprises RLMTQDCLQQRSKKKAAVV(K)-$C_{8-24}$ (SEQ ID NO: 9). In some embodiments, the peptide amphiphile comprises RTLAFVRFKKKAAVV(K)-$C_{8-24}$ (SEQ ID NO: 10).

In some embodiments, provided herein are nanofibers comprising the self-assembled TF-targeted peptide amphiphiles described herein.

In some embodiments, the nanofibers described herein further comprise filler peptide amphiphiles, wherein the filler peptide amphiphiles do not comprise a bioactive moiety. In some embodiments, the filler peptide amphiphiles comprise a hydrophobic non-peptide tail, a structured peptide segment, and a charged peptide segment. In some embodiments, the hydrophobic non-peptide tail comprises an 8-24 carbon alkyl chain ($C_{8-24}$). In some embodiments, the filler peptide amphiphile comprises a K residue, and wherein the hydrophobic non-peptide tail is attached to the sidechain of the K residue. In some embodiments, the structured peptide segment comprises VVAA (SEQ ID NO: 4) or any suitable combination or V and/or A residues. In some embodiments, the structured peptide segment has propensity to form β-sheet-like structures with adjacent structured peptide segments. In some embodiments, the charged peptide segment comprises an acidic, basic, or zwitterionic peptide segment. In some embodiments, the charged peptide segment comprises EE or KK. In some embodiments, the filler peptide amphiphile comprises KKAAVV(K)-$C_{8-24}$ (SEQ ID NO: 5).

In some embodiments, the nanofibers described herein further comprise a therapeutic peptide amphiphile displaying a therapeutic moiety. In some embodiments, the therapeutic peptide amphiphiles comprise a hydrophobic non-peptide tail, a structured peptide segment, a charged peptide segment, and a therapeutic moiety. In some embodiments, the hydrophobic non-peptide tail comprises an 8-24 carbon alkyl chain ($C_{8-24}$). In some embodiments, the therapeutic peptide amphiphile comprises a K residue, and wherein the hydrophobic non-peptide tail is attached to the sidechain of the K residue. In some embodiments, the structured peptide segment comprises VVAA (SEQ ID NO: 4) or any suitable combination or V and/or A residues. In some embodiments, the structured peptide segment has propensity to form β-sheet-like structures with adjacent structured peptide segments. In some embodiments, the charged peptide segment comprises an acidic, basic, or zwitterionic peptide segment. In some embodiments, the charged peptide segment comprises EE or KK. In some embodiments, the therapeutic peptide amphiphile comprises KKAAVV(K)-C$_{8-24}$ (SEQ ID NO: 5). In some embodiments, the therapeutic moiety is a procoagulant agent. In some embodiments, the procoagulant moiety is thrombin. In some embodiments, the procoagulant moiety is shielded to inhibit the bioactivity of the procoagulant moiety until a shielding moiety is removed. In some embodiments, the procoagulant moiety is thrombin and the shielding moiety is Factor X.

In some embodiments, a therapeutic agent (e.g., thrombin, peptide, etc.) is attached to the TF-targeted PAs and/or nanofibers non-covalently (e.g., electrostatic interaction) or covalently (e.g., via a linker (e.g., PEG linker, alkyl linker, peptide linker, etc.).

In some embodiments, provided herein are methods of treating or preventing hemorrhage in a subject comprising administering a TF-targeted nanofiber described herein (e.g., comprising filler PAs and/or therapeutic PAs) to a subject suffering from an acute injury. In some embodiments, the nanofiber is pharmaceutically formulated. In some embodiments, the nanofiber is administered by injection to a hemorrhagic or potentially-hemorrhagic site. In some embodiments, the nanofiber is co-administered with one or more additional treatments or therapies for hemorrhage and/or the acute injury.

In some embodiments, provided herein are kits comprising TF-targeted nanofiber described herein (e.g., comprising filler PAs and/or therapeutic PAs), and one or more additional components for delivering the nanofiber, storing the nanofiber, and/or for the treatment of hemorrhage and/or an acute injury.

BRIEF DESCRIPTION OF THE DRAWINGS

FIGS. 3A-B. RLM and RTL TF-targeted peptides demonstrate concentration-dependent binding to recombinant TF in vitro. (FIG. 3A) Binding assay was performed to assess the binding of each peptide sequence to recombinant TF. Peptides were coated to the bottom of the plates. Coating with recombinant TF served as the positive control. Plates were incubated with 75 ng of recombinant TF, rinsed, and residual TF representing binding was detected using a primary anti-TF antibody and secondary horseradish peroxidase antibody. Both RTL and RLM peptides were found to bind TF more than the nonspecific peptide, EGR peptide, and negative control (*p<0.05). (FIG. 3B) Dilution testing with the RTL and RLM peptides revealed a concentration-dependent increase in binding to recombinant TF. Absorbance measured at 450 nm.

FIGS. 4A-C. TF-targeted nanofibers bind to areas of liver injury and reduce hemorrhage in a rat model of liver injury in vivo. (FIG. 4A) Fluorescent microscopy of injured and uninjured liver demonstrates binding of the EGR PA, RLM PA, and RTL PA nanofibers to the sites of liver injury but not to uninjured liver. The nanofibers appear to bind near the vascular structures. (FIG. 4B) Assessment of % blood loss over time for each treatment group shows that the EGR PA, RLM PA, and RTL PA nanofibers reduce blood loss over time. (FIG. 4C) Total % blood loss for each treatment group reveals a 53% reduction in blood loss with injection of the RTL PA nanofiber.

(FIG. 6A) Assessment of % blood loss over time revealed less blood loss with increasing RTL targeting ligand density. (FIG. 6B) Assessment of % total blood loss revealed less blood loss with the 10, 25, 50, and 75% RTL PA nanofiber compared to sham. Administration of the 100% RTL PA nanofiber resulted in less blood loss compared to both sham and the nonspecific PA nanofiber. (FIG. 6C) Mean arterial pressure (MAP) was similar for the sham, 10, 25, 50, and 75% RTL PA nanofiber-treated animals. Animals treated with nonspecific PA and 100% RTL PA nanofiber had lower MAP compared to the sham, while the 100% RTL PA nanofiber-treated animals had lower MAP compared to 10, 25, 50, and 75% RTL PA nanofiber-treated animals.

FIG. 9. Liver punch model: Photographs of (Panel A) 12 mm punch biopsy tool, (Panel B) punch being created in the liver, and (Panel C) punch injury in the left lobe of the liver; (Panel D) graph of percent blood loss from injury over time.

DEFINITIONS

Figure 1:
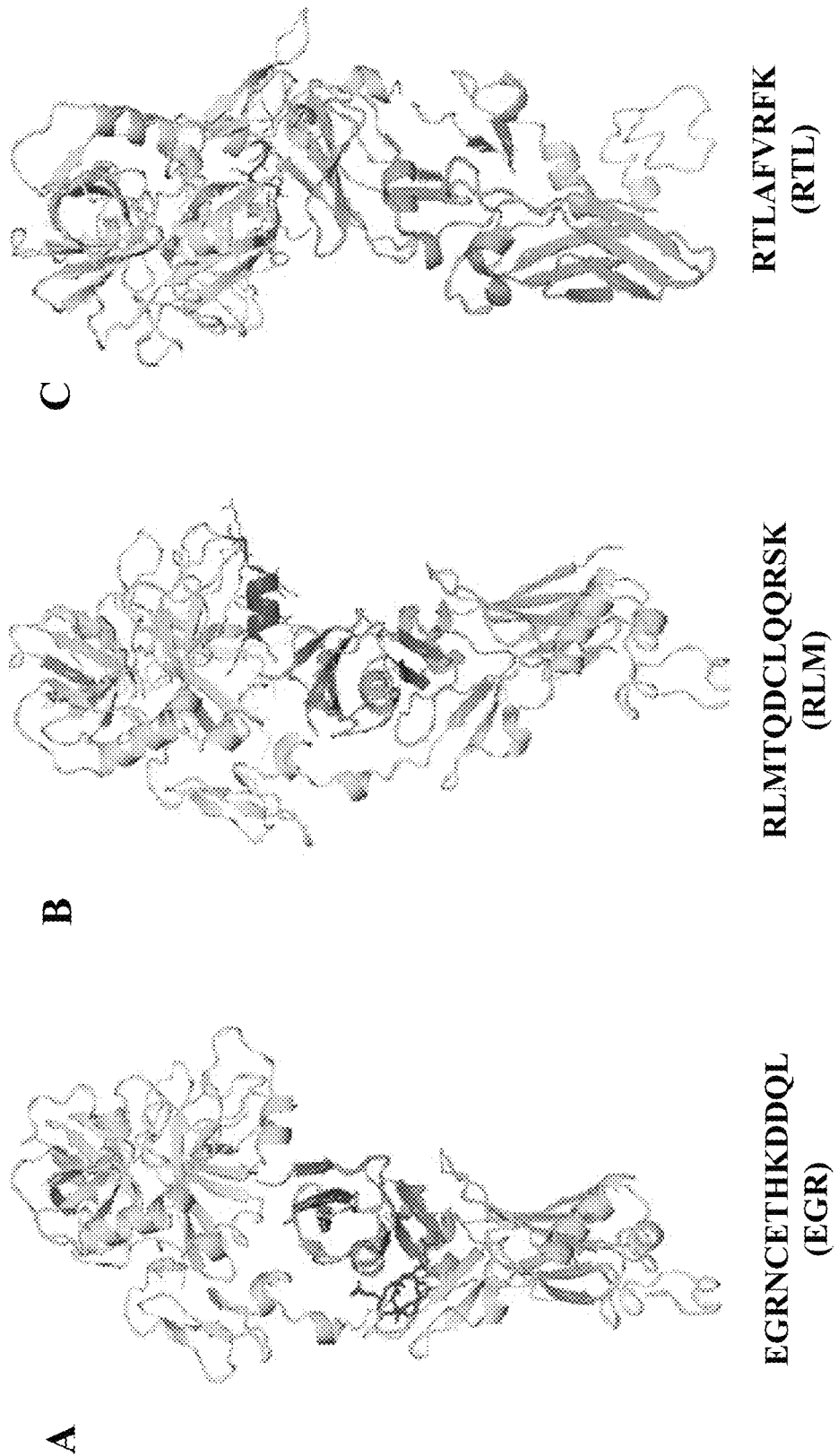
FIG. 1. Structural models of the interaction of TF with Factor VII. Protein models were produced using PyMol software (Schrodinger, Cambridge, Mass.), and the sequence was deposited in the National Center for Biotechnology Information Protein Data Bank for tissue factor (TF, blue) and Factor VII (yellow) (PDB #1DAN). (Panel A) EGRNCETHKDDQL (EGR) (SEQ ID NO: 1) found in the EGF-2 domain of Factor VII; (Panel B) RLMTQD-CLQQRSK (RLM) (SEQ ID NO: 2) found in the heavy chain of Factor VII; and (Panel C) RTLAFVRFK (RTL) (SEQ ID NO: 3) found in the heavy chain of Factor VII.

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a peptide amphiphile" is a reference to one or more peptide amphiphiles and equivalents thereof known to those skilled in the art, and so forth.

The term "amino acid" refers to natural amino acids, unnatural amino acids, and amino acid analogs, all in their D and L stereoisomers, unless otherwise indicated, if their structures allow such stereoisomeric forms.

Natural amino acids include alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), Lysine (Lys or K), methionine (Met or M), phenylalanine (Phe or F), proline (Pro or P), serine (Ser or S), threonine (Thr or T), tryptophan (Trp or W), tyrosine (Tyr or Y) and valine (Val or V).

Unnatural amino acids include, but are not limited to, azetidinecarboxylic acid, 2-aminoadipic acid, 3-aminoadipic acid, beta-alanine, naphthylalanine ("naph"), aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine ("tBuG"), 2,4-diaminoisobutyric acid, desmosine, 2,2'-diaminopimelic acid, 2,3-diaminopropionic acid, N-ethylglycine, N-ethylasparagine, homoproline ("hPro" or "homoP"), hydroxylysine, allo-hydroxylysine, 3-hydroxyproline ("3Hyp"), 4-hydroxyproline ("4Hyp"), isodesmosine, allo-isoleucine, N-methylalanine ("MeAla" or "Nime"), N-alkylglycine ("NAG") including N-methylglycine, N-methylisoleucine, N-alkylpentylglycine ("NAPG") including N-methylpentylglycine. N-methylvaline, naphthylalanine, norvaline ("Norval"), norleucine ("Norleu"), octylglycine ("OctG"), ornithine ("Orn"), pentylglycine ("pG" or "PGly"), pipecolic acid, thioproline ("ThioP" or "tPro"), homoLysine ("hLys"), and homoArginine ("hArg").

The term "amino acid analog" refers to a natural or unnatural amino acid where one or more of the C-terminal carboxy group, the N-terminal amino group and side-chain bioactive group has been chemically blocked, reversibly or irreversibly, or otherwise modified to another bioactive group. For example, aspartic acid-(beta-methyl ester) is an amino acid analog of aspartic acid; N-ethylglycine is an amino acid analog of glycine; or alanine carboxamide is an amino acid analog of alanine. Other amino acid analogs include methionine sulfoxide, methionine sulfone, S-(carboxymethyl)-cysteine, S-(carboxymethyl)-cysteine sulfoxide and S-(carboxymethyl)-cysteine sulfone.

As used herein, the term "peptide" refers an oligomer to short polymer of amino acids linked together by peptide bonds. In contrast to other amino acid polymers (e.g., proteins, polypeptides, etc.), peptides are of about 50 amino acids or less in length. A peptide may comprise natural amino acids, non-natural amino acids, amino acid analogs, and/or modified amino acids. A peptide may be a subsequence of naturally occurring protein or a non-natural (artificial) sequence.

As used herein, the term "artificial" refers to compositions and systems that are designed or prepared by man, and are not naturally occurring. For example, an artificial peptide, peptoid, or nucleic acid is one comprising a non-natural sequence (e.g., a peptide without 100% identity with a naturally-occurring protein or a fragment thereof).

As used herein, a "conservative" amino acid substitution refers to the substitution of an amino acid in a peptide or polypeptide with another amino acid having similar chemical properties, such as size or charge. For purposes of the present disclosure, each of the following eight groups contains amino acids that are conservative substitutions for one another:

1) Alanine (A) and Glycine (G);
2) Aspartic acid (D) and Glutamic acid (E);
3) Asparagine (N) and Glutamine (Q);
4) Arginine (R) and Lysine (K);
5) Isoleucine (I), Leucine (L), Methionine (M), and Valine (V);
6) Phenylalanine (F), Tyrosine (Y), and Tryptophan (W);
7) Serine (S) and Threonine (T); and
8) Cysteine (C) and Methionine (M).

Naturally occurring residues may be divided into classes based on common side chain properties, for example: polar positive (or basic) (histidine (H), lysine (K), and arginine (R)); polar negative (or acidic) (aspartic acid (D), glutamic acid (E)); polar neutral (serine (S), threonine (T), asparagine (N), glutamine (Q)); non-polar aliphatic (alanine (A), valine (V), leucine (L), isoleucine (I), methionine (M)); non-polar aromatic (phenylalanine (F), tyrosine (Y), tryptophan (W)); proline and glycine; and cysteine. As used herein, a "semi-conservative" amino acid substitution refers to the substitution of an amino acid in a peptide or polypeptide with another amino acid within the same class.

In some embodiments, unless otherwise specified, a conservative or semi-conservative amino acid substitution may also encompass non-naturally occurring amino acid residues that have similar chemical properties to the natural residue. These non-natural residues are typically incorporated by chemical peptide synthesis rather than by synthesis in biological systems. These include, but are not limited to, peptidomimetics and other reversed or inverted forms of amino acid moieties. Embodiments herein may, in some embodiments, be limited to natural amino acids, non-natural amino acids, and/or amino acid analogs.

Non-conservative substitutions may involve the exchange of a member of one class for a member from another class.

As used herein, the term "sequence identity" refers to the degree of which two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) differ only by conservative and/or semi-conservative amino acid substitutions. The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

Any polypeptides described herein as having a particular percent sequence identity or similarity (e.g., at least 70%) with a reference sequence ID number, may also be expressed as having a maximum number of substitutions (or terminal deletions) with respect to that reference sequence. For example, a sequence having at least Y % sequence identity (e.g., 90%) with SEQ ID NO:Z (e.g., 100 amino acids) may have up to X substitutions (e.g., 10) relative to SEQ ID NO:Z, and may therefore also be expressed as "having X (e.g., 10) or fewer substitutions relative to SEQ ID NO:Z."

As used herein, the term "nanofiber" refers to an elongated or threadlike filament (e.g., having a significantly greater length dimension that width or diameter) with a diameter typically less than 100 nanometers.

As used herein, the term "supramolecular" (e.g., "supramolecular complex," "supramolecular interactions," "supramolecular fiber," "supramolecular polymer," etc.) refers to the non-covalent interactions between molecules (e.g., polymers, marcomolecules, etc.) and the multicomponent assemblies, complexes, systems, and/or fibers that form as a result.

As used herein, the terms "self-assemble" and "self-assembly" refer to formation of a discrete, non-random, aggregate structure from component parts; said assembly occurring spontaneously through random movements of the components (e.g. molecules) due only to the inherent chemical or structural properties and attractive forces of those components.

As used herein, the term "peptide amphiphile" refers to a molecule that, at a minimum, includes a non-peptide lipophilic (hydrophobic) segment, a structural peptide segment and/or charged peptide segment (often both), and optionally a bioactive segment (e.g., linker segment, bioactive segment, etc.). The peptide amphiphile may express a net charge at physiological pH, either a net positive or negative net charge, or may be zwitterionic (i.e., carrying both positive and negative charges). Certain peptide amphiphiles consist of or comprise: (1) a hydrophobic, non-peptide segment (e.g., comprising an acyl group of six or more carbons), (2) a structural peptide segment (e.g., β-sheet forming); (3) a charged peptide segment, and (4) a bioactive segment (e.g., linker segment).

As used herein and in the appended claims, the term "lipophilic moiety" or "hydrophobic moiety" refers to the moiety (e.g., an acyl, ether, sulfonamide, or phosphodiestermoiety) disposed on one terminus (e.g., C-terminus, N-terminus) of the peptide amphiphile, and may be herein and elsewhere referred to as the lipophilic or hydrophobic segment or component. The hydrophobic segment should be of a sufficient length to provide amphiphilic behavior and aggregate (or nanosphere or nanofiber) formation in water or another polar solvent system. Accordingly, in the context of the embodiments described herein, the hydrophobic component preferably comprises a single, linear acyl chain of the formula: $C_{n-1}H_{2n-1}C(O)$— where n=2-25. In some embodiments, a linear acyl chain is the lipophilic group (saturated or unsaturated carbons), palmitic acid. However, other lipophilic groups may be used in place of the acyl chain such as steroids, phospholipids and fluorocarbons.

As used herein, the term "structural peptide" refers to a portion of a peptide amphiphile, typically disposed between the hydrophobic segment and the charged peptide segment. The structural peptide is generally composed of three to ten amino acid residues with non-polar, uncharged side chains (e.g., His (H), Val (V), Ile (I), Leu (L), Ala (A), Phe (F)) selected for their propensity to form hydrogen bonds or other stabilizing interactions (e.g., hydrophobic interactions, van der Waals' interactions, etc.) with structural segments of adjacent structural segments. In some embodiments, nanofibers of peptide amphiphiles having structural peptide segments display linear or 2D structure when examined by microscopy and/or α-helix and/or β-sheet character when examined by circular dichroism (CD).

As used herein, the term "beta (β)-sheet-forming peptide segment" refers to a structural peptide segment that has a propensity to display β-sheet-like character (e.g., when analyzed by CD). In some embodiments, amino acids in a beta (β)-sheet-forming peptide segment are selected for their propensity to form a beta-sheet secondary structure. Examples of suitable amino acid residues selected from the twenty naturally occurring amino acids include Met (M), Val (V), Ile (I), Cys (C), Tyr (Y), Phe (F), Gln (Q), Leu (L), Thr (T), Ala (A), and Gly (G) (listed in order of their propensity to form beta sheets). However, non-naturally occurring amino acids of similar beta-sheet forming propensity may also be used. Peptide segments capable of interacting to form beta sheets and/or with a propensity to form beta sheets are understood (See, e.g., Mayo et al. Protein Science (1996), 5:1301-1315; herein incorporated by reference in its entirety).

As used herein, the term "charged peptide segment" refers to a portion of a peptide amphiphile that is rich (e.g., >50%, >75%, etc.) in charged amino acid residues, or amino acid residue that have a net positive or negative charge under physiologic conditions. A charged peptide segment may be acidic (e.g., negatively charged), basic (e.g., positively charged), or zwitterionic (e.g., having both acidic and basic residues).

As used herein, the terms "carboxy-rich peptide segment," "acidic peptide segment," and "negatively-charged peptide segment" refer to a peptide sequence of a peptide amphiphile that comprises one or more amino acid residues that have side chains displaying carboxylic acid side chains (e.g., Glu (E), Asp (D), or non-natural amino acids). A carboxy-rich peptide segment may optionally contain one or more additional (e.g., non-acidic) amino acid residues. Non-natural amino acid residues, or peptidomimetics with acidic side chains could be used, as will be evident to one ordinarily skilled in the art. There may be from about 2 to about 7 amino acids, and or about 3 or 4 amino acids in this segment.

As used herein, the terms "amino-rich peptide segment", "basic peptide segment," and "positively-charged peptide segment" refer to a peptide sequence of a peptide amphiphile that comprises one or more amino acid residues that have side chains displaying positively-charged acid side chains (e.g., Arg (R), Lys (K), His (H), or non-natural amino acids, or peptidomimetics). A basic peptide segment may optionally contain one or more additional (e.g., non-basic) amino acid residues. Non-natural amino acid residues with basic side chains could be used, as will be evident to one ordinarily skilled in the art. There may be from about 2 to about 7 amino acids, and or about 3 or 4 amino acids in this segment.

As used herein, the term "bioactive peptide" refers to amino acid sequences that mediate the action of sequences, molecules, or supramolecular complexes associated therewith. Peptide amphiphiles and structures (e.g., nanofibers) bearing bioactive peptides (e.g., a TF-targeting sequence, etc.) exhibits the functionality of the bioactive peptide.

The term "effective dose" or "effective amount" refers to an amount of an agent that results in the reduction of symptoms in a patient or results in a desired biological outcome (e.g., cessation of bleeding).

As used herein, the terms "administration" and "administering" refer to the act of giving/taking a drug, prodrug, or other agent, or therapeutic to/by a subject or in vivo, in vitro, or ex vivo cells, tissues, and organs. Exemplary routes of administration to the human body can be through space under the arachnoid membrane of the brain or spinal cord (intrathecal), the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

The term "treatment" encompasses both therapeutic and prophylactic/preventative measures unless otherwise indicated. Those in need of treatment include, but are not limited to, individuals already having a particular condition as well as individuals who are at risk of acquiring a particular condition or disorder (e.g., those having a genetic or epigenetic predisposition; based on age, gender, lifestyle, etc.). The term "treating" refers to administering an agent to a subject for therapeutic and/or prophylactic/preventative purposes.

As used herein, the terms "co-administration" and "co-administering" refer to the administration of at least two agent(s) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

DETAILED DESCRIPTION

Provided herein are tissue factor (TF)-targeted nanofibers and methods of treating hemorrhage in a subject therewith. In particular, peptide amphiphiles (PAs) are provided that comprise a TF-targeting peptide sequence and self-assemble under aqueous conditions into PA nanofibers displaying the TF-targeting sequence on the exterior of the nanofiber.

Tissue factor (TF) is an integral membrane protein found in the adventitial cells of all blood vessels larger than capillaries and is only exposed to the circulating blood elements within the intravascular space following disruption of the vessel (ref. 9; herein incorporated by reference in its entirety).

Peptide amphiphiles (PA) are structural units comprising: a hydrophobic tail (e.g., an alkyl group), a structural domain (e.g., β-sheet forming peptide domain), and a bioactive peptide segment; suitable PAs self-assemble under aqueous conditions to for supramolecular nanostructures (e.g., nanofibers) (refs 10-13; herein incorporated by reference in their entireties).

In experiments conducted during development of embodiments herein, TF-targeting sequences were incorporated into PAs. Nanofiber formation, localization within an in vivo animal model of hemorrhage, and effect on blood loss were analyzed. Experiments demonstrated that TF-targeted PA nanofibers specifically bind to the site of hemorrhage and reduce blood loss.

Unexpectedly, experiments conducted during development of embodiments herein demonstrated that TF-targeted nanofibers without a therapeutic molecule or peptide specifically directed to treat hemorrhage (e.g., a thrombin peptide), provide useful treatment for hemorrhage. Without being bound by theory, an explanation for this effect is that the localized presence of the nanofibers at the hemorrhage site contributes to the ability of clotting factors, fibrin, fibrinogen, platelets, etc. to adhere to sites of injury. Supporting this concept, experiments described herein demonstrated that platelets bind to a nanofiber network formed by the PA in vitro. Experiments also demonstrated that the RTL PA nanofiber reduces free fibrinogen levels in whole blood, indicating that the RTL PA nanofiber is binding to fibrinogen. Together these data indicate that in vivo platelets and fibrinogen adhere to the RTL PA nanofiber at the site of injury, further potentiating coagulation at the site of hemorrhage; however, embodiments herein are not limited to any particular mechanism of action and an understanding of the mechanism of action is not necessary to practice such embodiments.

Although TF-targeted PA nanofibers alone provide therapeutic benefit to hemorrahage, the construction of the PA nanofibers also allows delivery of a therapeutic payload. In some embodiments, this therapeutic payload is protected from systemic exposure until it is triggered to be released at the site of hemorrhage. For example, in some embodiments, thrombin or a thrombin mimetic is incorporated into TF-targeted nanofibers to increase the therapeutic potency and/or provide an alternative mechanism within the same system for treating hemorrhages.

The TF-targeted PA nanofibers described herein provide numerous advantages inducing being a rapidly deployable, temperature stable, and easily injectable therapy to attenuate non-compressible hemorrhage in the far forward setting. In some embodiments, TF-targeted PA nanofibers are injected intravenously and are specifically targeted to the site of hemorrhage to stop bleeding.

In some embodiments, the peptide amphiphile molecules and compositions of the embodiments described herein are synthesized using preparatory techniques well-known to those skilled in the art, preferably, by standard solid-phase peptide synthesis, with the addition of a fatty acid in place of a standard amino acid at the N-terminus (or C-terminus) of the peptide, in order to create the lipophilic segment (although in some embodiments, alignment of nanofibers is performed via techniques not previously disclosed or used in the art (e.g., extrusion through a mesh screen). Synthesis typically starts from the C-terminus, to which amino acids are sequentially added using either a Rink amide resin (resulting in an —NH2 group at the C-terminus of the peptide after cleavage from the resin), or a Wang resin (resulting in an —OH group at the C-terminus). Accordingly, embodiments described herein encompasses peptide amphiphiles having a C-terminal moiety that may be selected from the group consisting of —H, —OH, —COOH, —CONH2, and —NH2.

In some embodiments, peptide amphiphiles comprise a hydrophobic (non-peptide) segment linked to a peptide. In some embodiments, the peptide comprises a structural segment (e.g., hydrogen-bond-forming segment, beta-sheet-forming segment, etc.), and a charged segment (e.g., acidic segment, basic segment, zwitterionic segment, etc.). In some embodiments, the peptide further comprises linker or spacer segments for adding solubility, flexibility, distance between segments, etc. In some embodiments, peptide amphiphiles comprise a spacer segment (e.g., peptide and/or non-peptide spacer) at the opposite terminus of the peptide from the hydrophobic segment. In some embodiments, the spacer segment comprises peptide and/or non-peptide elements. In some embodiments, the spacer segment comprises one or more bioactive groups (e.g., alkene, alkyne, azide, thiol, etc.). In some embodiments, various segments may be connected by linker segments (e.g., peptide (e.g., GG) or non-peptide (e.g., alkyl, OEG, PEG, etc.) linkers).

The lipophilic or hydrophobic segment is typically incorporated at the N- or C-terminus of the peptide after the last amino acid coupling, and is composed of a fatty acid or other acid that is linked to the N- or C-terminal amino acid through an acyl bond. In aqueous solutions, PA molecules self-assemble (e.g., into cylindrical micelles (a.k.a nanofibers)) that bury the lipophilic segment in their core and display the bioactive peptide on the surface. The structural peptide undergoes intermolecular hydrogen bonding to form beta sheets that orient parallel to the long axis of the micelle.

In some embodiments, compositions described herein comprise PA building blocks that in turn comprise a hydrophobic segment and a peptide segment. In certain embodiments, a hydrophobic (e.g., hydrocarbon and/or alkyl/alkenyl/alkynyl tail, or steroid such as cholesterol) segment of sufficient length (e.g., 2 carbons, 3 carbons, 4 carbons, 5 carbons, 6 carbons, 7 carbons, 8 carbons, 9 carbons, 10 carbons, 11 carbons, 12 carbons, 13 carbons, 14 carbons, 15 carbons, 16 carbons, 17 carbons, 18 carbons, 19 carbons, 20 carbons, 21 carbons, 22 carbons, 23 carbons, 24 carbons, 25 carbons, 26 carbons, 27 carbons, 28 carbons, 29 carbons, 30 carbons or more, or any ranges there between) is covalently coupled to peptide segment (e.g., a peptide comprising a segment having a preference for beta-strand conformations or other supramolecular interactions) to yield a peptide amphiphile molecule. In some embodiments, a plurality of such PAs will self-assemble in water (or aqueous solution) into a nanostructure (e.g., nanofiber). In various embodiments, the relative lengths of the peptide segment and hydrophobic segment result in differing PA molecular shape and nanostructural architecture. For example, a broader peptide segment and narrower hydrophobic segment results in a generally conical molecular shape that has an effect on the assembly of PAs (See, e.g., J. N. Israelachvili Intermolecular and surface forces; 2nd ed.; Academic: London San Diego, 1992; herein incorporated by reference in its entirety). Other molecular shapes have similar effects on assembly and nanostructural architecture.

In some embodiments, to induce self-assembly of an aqueous solution of peptide amphiphiles, the pH of the solution may be changed (raised or lowered) or multivalent ions, such as calcium, or charged polymers or other macromolecules may be added to the solution.

In some embodiments, the hydrophobic segment is a non-peptide segment (e.g., alkyl/alkenyl/alkynyl group). In some embodiments, the hydrophobic segment comprises an alkyl chain (e.g., saturated) of 4-25 carbons (e.g., 4, 5, 6, 7, 8, 9, 10, 11, 12, 13, 14, 15, 16, 17, 18, 19, 20, 21, 22, 23, 24, 25), fluorinated segments, fluorinated alkyl tails, heterocyclic rings, aromatic segments, pi-conjugated segments, cycloalkyls, oligothiophenes etc. In some embodiments, the hydrophobic segment comprises an acyl/ether chain (e.g., saturated) of 2-30 carbons (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30).

In some embodiments, PAs comprise one or more peptide segments. Peptide segment may comprise natural amino acids, modified amino acids, unnatural amino acids, amino acid analogs, peptidomimetics, or combinations thereof. In some embodiments, peptide segment comprise at least 50% sequence identity or similarity (e.g., conservative or semi-conservative) to one or more of the peptide sequences described herein.

In some embodiments, peptide amphiphiles comprise a charged peptide segment. The charged segment may be acidic, basic, or zwitterionic.

In some embodiments, peptide amphiphiles comprise an acidic peptide segment. For example, in some embodiments, the acidic peptide comprises one or more (e.g., 1, 2, 3, 4, 5, 6, 7, or more) acidic residues (D and/or E) in sequence. In some embodiments, the acidic peptide segment comprises up to 7 residues in length and comprises at least 50% acidic residues. In some embodiments, an acidic peptide segment comprises $(Xa)_{1-7}$, wherein each Xa is independently D or E. In some embodiments, an acidic peptide segment comprises EE.

In some embodiments, peptide amphiphiles comprise a basic peptide segment. For example, in some embodiments, the acidic peptide comprises one or more (e.g., 1, 2, 3, 4, 5, 6, 7, or more) basic residues (R, H, and/or K) in sequence. In some embodiments, the basic peptide segment comprises up to 7 residues in length and comprises at least 50% basic residues. In some embodiments, an acidic peptide segment comprises $(Xb)_{1-7}$, wherein each Xb is independently R, H, and/or K.

In some embodiments, peptide amphiphiles comprises a structural and/or beta-sheet-forming segment. In some embodiments, the structural segment is rich in H, I, L, F, V, and A residues. In some embodiments, the structural and/or beta-sheet-forming segment comprises an alanine- and valine-rich peptide segment (e.g., AAVV (SEQ ID NO: 6), AAAVVV (SEQ ID NO: 7), or other combinations of V and A residues, etc.). In some embodiments, the structural and/or beta sheet peptide comprises 4 or more consecutive A and/or V residues, or conservative or semi-conservative substitutions thereto. In some embodiments, the structural and/or beta-sheet forming peptide segment comprises 4 or more consecutive non-polar aliphatic residues (e.g., alanine (A), valine (V), leucine (L), isoleucine (I), methionine (M)). In some embodiments, the structural and/or beta-sheet forming peptide segment comprises 2-16 amino acids in length and comprises 4 or more (e.g., 2, 3, 4, 5, 6, 7, 8, 9, 10, 11, 12, 13, 14, 15, 16, or ranges there between) non-polar aliphatic residues.

In some embodiments, peptide amphiphiles comprise a non-peptide spacer or linker segment. In some embodiments, the non-peptide spacer or linker segment is located at the opposite terminus of the peptide from the hydrophobic segment. In some embodiments, the spacer or linker segment provides the attachment site for a bioactive group. In some embodiments, the spacer or linker segment provides a reactive group (e.g., alkene, alkyne, azide, thiol, maleimide etc.) for functionalization of the PA. In some embodiments, the spacer or linker is a substantially linear chain of CH2, O, $(CH_2)_2O$, $O(CH_2)_2$, NH, and C=O groups (e.g., CH2(O $(CH_2)_2)_2$NH, $CH_2(O(CH_2)_2)_2NHCO(CH_2)_2CCH$, etc.). In some embodiments, a spacer or linker further comprises additional bioactive groups, substituents, branches, etc.

Suitable peptide amphiphiles, PA segments, PA nanostructures, and associated reagents and methods are described, for example in U.S. Pat. Nos. 8,512,693; 8,450,271; 8,138,140; 8,124,583; 8,114,835; 8,114,834; 8,080,262; 8,063,014; 7,851,445; 7,838,491; 7,745,708; 7,683,025; 7,554,021; 7,544,661; 7,534,761; 7,491,690; 7,452,679; 7,390,526; 7,371,719; 6,890,654; herein incorporated by reference in their entireties.

The characteristics (e.g., shape, rigidity, hydrophilicity, etc.) of a PA supramolecular structure depend upon the identity of the components of a peptide amphiphile (e.g., lipophilic segment, acidic segment, structural segment, bioactive segment, etc.). For example, nanofibers, nanospheres, intermediate shapes, and other supramolecular structures are achieved by adjusting the identity of the PA component parts. In some embodiments, characteristics of supramolecular nanostructures of PAs are altered by post-assembly manipulation (e.g., heating/cooling, stretching, etc.).

In some embodiments, a peptide amphiphile comprises: (a) a hydrophobic tail comprising an alkyl chain of 8-24 carbons; (b) a structural segment (e.g., comprising VVAA (SEQ ID NO: 4)); and (c) a charged segment (e.g., comprising KK, EE, etc). In some embodiments, any PAs within the scope described herein, comprising the components described herein, or within the skill of one in the field, may find use herein.

In some embodiments, peptide amphiphiles comprise a bioactive moiety. In particular embodiments, a bioactive moiety is the C-terminal or N-terminal most segment of the PA. In some embodiments, the bioactive moiety is attached to the end of the charged segment. In some embodiments, the bioactive moiety is exposed on the surface of an assembled PA structure (e.g., nanofiber). A bioactive moiety is typically a peptide (e.g., TF-targeting peptide, etc.), but is not limited thereto. Examples described in detail herein utilize a peptide sequence that binds tissue factor as a bioactive moiety. In some embodiments, a bioactive peptide is a therapeutic peptide. Bioactive peptides and other moieties for achieving functionality will be understood. In some embodiments, bioactive moieties are provided having binding affinity for a target protein (e.g., tissue factor). The binding affinity ($K_d$) may be chosen from one of: less than 10 µM, less than 1 µM, less than 100 nM, less than 10 nM, less than 1 nM, less than 100 µM.

In some embodiments, the bioactive peptide is a TF-targeting peptide. Suitable examples include EGRNCETH-KDDQL (SEQ ID NO: 1), RLMTQDCLQQRSK (SEQ ID NO: 2), and RTLAFVRFK (SEQ ID NO: 3). In some embodiments, a bioactive peptide binds TF and has at least 70% (e.g., 70%, 75%, 80%, 85%, 90%, 95%, 100%, or more, or ranges therebetween) sequence identity with one of SEQ ID NO: 1, 2, or 3. In some embodiments, a bioactive peptide binds TF and has at least 70% (e.g., 70%, 75%, 80%, 85%, 90%, 95%, 100%, or more, or ranges therebetween) sequence similarity (e.g., conservative or semi-conservative) with one of SEQ ID NO: 1, 2, or 3. In some embodiments, a bioactive peptide binds TF and has 8 or fewer (e.g., 8, <8, 7, <7, 6, <6, 5, <5, 4, <4, 3, <3, 2, <2, 1, 0) substitutions relative to SEQ ID NO: 1, 2, or 3. In some embodiments, a bioactive peptide binds TF and has 8 or fewer (e.g., 8, <8, 7, <7, 6, <6, 5, <5, 4, <4, 3, <3, 2, <2, 1, 0) non-conservative substitutions relative to SEQ ID NO: 1, 2, or 3. In some embodiments, a bioactive peptide binds TF and has 8 or fewer (e.g., 8, <8, 7, <7, 6, <6, 5, <5, 4, <4, 3, <3, 2, <2, 1, 0) semi-conservative substitutions relative to SEQ ID NO: 1, 2, or 3. In some embodiments, a bioactive peptide binds TF and has 8 or fewer (e.g., 8, <8, 7, <7, 6, <6, 5, <5, 4, <4, 3, <3, 2, <2, 1, 0) conservative substitutions relative to SEQ ID NO: 1, 2, or 3.

In some embodiments, a peptide amphiphile comprises: (a) a hydrophobic tail comprising an alkyl chain of 8-24 carbons; (b) a structural segment (e.g., comprising VVAA (SEQ ID NO: 4), AAVV (SEQ ID NO: 6), VA, AV, etc.); (c) a charged segment (e.g., comprising KK, EE, EK, KE, etc.), and a bioactive peptide (e.g., TF-targeting peptide). In some embodiments, a PA further comprises an attachment segment or residue (e.g., K) for attachment of the hydrophobic tail to the peptide portion of the PA. In some embodiments, the hydrophobic tail is attached to a lysine side chain.

In some embodiments, a peptide amphiphile comprises (e.g., from C-terminus to N-terminus or from N-terminus to C-terminus): bioactive peptide (e.g., TF-targeting peptide)—charged segment (e.g., comprising KK, EE, EK, KE, etc.)—structural segment (e.g., comprising VVAA (SEQ ID NO: 4), AAVV (SEQ ID NO: 6), VA, AV, etc.)—hydrophobic tail (e.g., comprising an alkyl chain of 8-24 carbons).

In some embodiments, a peptide amphiphile comprises (e.g., from C-terminus to N-terminus or from N-terminus to C-terminus): bioactive peptide (e.g., TF-targeting peptide)—charged segment (e.g., comprising KK, EE, EK, KE, etc.)—structural segment (e.g., comprising VVAA (SEQ ID NO: 4), AAVV (SEQ ID NO: 6), VA, AV, etc.)—attachment segment or peptide (e.g., K)—hydrophobic tail (e.g., comprising an alkyl chain of 8-24 carbons).

In some embodiments, a peptide amphiphile comprises (e.g., from C-terminus to N-terminus or from N-terminus to C-terminus): bioactive peptide (e.g., TF-targeting peptide)—KKAAVV(K) (SEQ ID NO: 5)—hydrophobic tail (e.g., comprising an alkyl chain of 8-24 carbons). In some embodiments, the hydrophobic tail is attached to the (K) sidechain. In some embodiments, a peptide amphiphile comprises EGRNCETHKDDQLKKAAVV(K)-$C_{8-24}$ (SEQ ID NO: 8). In some embodiments, a peptide amphiphile comprises RLMTQDCLQQRSKKKAAVV(K)-$C_{8-24}$ (SEQ ID NO: 9). In some embodiments, a peptide amphiphile comprises RTLAFVRFKKKAAVV(K)-$C_{8-24}$ (SEQ ID NO: 10).

In some embodiments, provided herein are nanofibers and nanostructures assembled from the peptide amphiphiles described herein. In some embodiments, a nanofiber is prepared by the self-assembly of the PAs described herein. In some embodiments, a nanofiber comprises or consists of PAs displaying a TF-targeting peptide. In some embodiments, the TF-targeting peptides are displayed on the surface of the nanofiber. In some embodiments, in addition to PAs displaying TF-targeting peptides, filler PAs are included in the nanofibers. In some embodiments, filler PAs are peptide amphiphiles, as described herein (e.g., structural segment, charged segment, hydrophobic segment, etc.), but lacking a bioactive moiety. In some embodiments, the filler PAs and TF-targeting PAs self-assemble into a nanofiber comprising both types of PAs. In some embodiments, nanostructures (e.g., nanofibers) assembled from the peptide amphiphiles described herein are provided.

In some embodiments, nanostructures are assembled from (1) PAs bearing a bioactive moiety (e.g., TF-bonding moiety) and (2) filler PAs (e.g., PAs not-labeled or not displaying a bioactive moiety, etc.). In some embodiments, nanostructures (e.g., nanofibers) comprise: (i) less than 50% (e.g., 49%, 45%, 40%, 35%, 30%, 25%, 20%, 15%, 10%, 5%, 4%, 3%, 2%, 1%, or any ranges there between) PAs bearing a bioactive moiety (e.g., TF-targeting moiety). In some embodiments, nanostructures (e.g., nanofibers) comprise and at least 2% (e.g., 2%, 3%, 4%, 5%, 10%, 15%, 20%, 25%, 30%, 35%, 40%, 45%, 50%, 55%, 60%, 65%, 70%, 75%, 80%, 85%, 90%, 95%, 98%, or any ranges there between) PAs bearing a bioactive moiety (e.g., TF-targeting moiety). In some embodiments, nanofibers comprise at least 50% (e.g., 50%, 55%, 60%, 65%, 70%, 75%, 80%, 85%, 90%, 95%, 98%, or any ranges there between) filler peptide amphiphiles. In some embodiments, the ratio of PAs bearing a bioactive moiety to filler PAs determines the density of bioactive moieties (e.g., TF-targeting moiety) displayed on the nanostructure surface.

In some embodiments, nanofibers additionally comprise PAs bearing bioactive moieties other than TF-targeting moieties. For example, in some embodiments, nanofibers comprise filler PAs, PAs bearing TF-targeting moieties, and PAs bearing a therapeutic moiety. In some embodiments, a therapeutic moiety is a peptide, antibody, nucleic acid (e.g., antisense RNA, siRNA, etc.), small molecule, etc. In some embodiments, a therapeutic moiety is a bioactive peptide. In some embodiments, nanostructures (e.g., nanofibers) comprise: (i) less than 50% (e.g., 49%, 45%, 40%, 35%, 30%, 25%, 20%, 15%, 10%, 5%, 4%, 3%, 2%, 1%, or any ranges there between) PAs bearing a therapeutic moiety.

In some embodiments, a therapeutic moiety is a procoagulant moiety. In some embodiments, a procoagulant moiety is a material or polymer that promotes coagulation when delivered to a site of bleeding or hemorrhage. For example, the material or polymer provides a surface that enhances the ability of clotting factors, fibrin, fibrinogen, platelets, etc. to adhere to sites of injury, thereby potentiating coagulation. In such embodiments, endogenous coagulation factors, enzymes, proteins, and/or other components of a subject's endogenous clotting cascade concentrate on the material or polymer, and thereby coagulation is enhanced at the site. In other embodiments, a procoagulant moiety is a coagulation factor, enzyme, protein, and/or other component of the clotting cascade. In such embodiments, the TF-targeted nanofibers deliver the exogenous promoters of coagulation (e.g., exogenous components of the clotting cascade) to the site of bleeding or hemorrhage, thereby promoting clot formation and cessation of bleeding or hemorrhage. Exemplary procoagulant moieties include, but are not limited to, silica, zeolite, polysaccharides, starch, chitin and its derivatives, sorbent polymers, kaolin, celite, alum, thrombin, fibrinogen, fibrin, alginate, recombinant factor VIIa, diatomaceous earth, carbon, von Willebrand factor, fibronectin, vitronectin, thromboxane A2, thrombopoietin, intracellular adhesion molecule (ICAM)-1 and -2, vascular cell adhesion molecule (VCAM), aggretin, adenosine-di-phosphate (ADP), Ristocetin, collagen, cationic chitosan salts (e.g., chitosan formate, chitosan acetate, chitosan lactate, chitosan maliate, chitosan chloride, chitosan ascorbate, chitosan citrate, etc.), etc.

In some embodiments, a therapeutic moiety is a protected or shielded therapeutic moiety. In such embodiments, the therapeutic moiety is prevented from exerting bioactivity (e.g., therapeutic action) until a protecting group or shielding group is removed. In some embodiments, a protecting or shielding group is a moiety that is cleavable and/or removable at the site of bleeding or hemorrhage. For example, in some embodiments, a therapeutic moiety is shielded from exerting its bioactivity by Factor X (e.g., the therapeutic moiety is shielded and inactive as long as Factor X is present on the therapeutic moiety of the nanofiber). Factor X is a component of the clotting cascade that is converted to Factor Xa by Factor IXa or the factor VIIa/TF complex. Factor IXa and VIIa are only present at the sites of active hemorrhage. Thus, by protecting the therapeutic moiety with Factor X, the therapeutic moiety remains inactive until the nanofibers are deliverer to the site of hemorrhage (e.g., by TF-targetting). This approach ensures that the therapeutic moiety becomes active once the nanofiber binds to the site of active hemorrhage.

In some embodiments, the therapeutic moiety is thrombin or a fragment thereof with pro-clotting and/or pro-coagulation bioactivity. Thrombin (EC 3.4.21.5) is a serine protease thatis encoded by the F2 gene in humans. Prothrombin (coagulation factor II) is proteolytically cleaved to form thrombin in the coagulation cascade, the clotting process. Thrombin in turn acts as a serine protease that converts soluble fibrinogen into insoluble strands of fibrin, as well as catalyzing many other coagulation-related reactions. In some embodiments, thrombin is conjugated to the nanofibers herein for delivery to treatment sites. In some embodiments, peptide amphiphiles are provided comprising a hydrophobic tail, a structural peptide, a charged peptide, and a bioactive thrombin polypeptide or peptide (e.g., full-length thrombin or a bioactive fragment or variant thereof). In some embodiments, the therapeutic moiety is a protected thrombin or shielded thrombin. In some embodiments, a protected thrombin is prothrombin (e.g., inactive version of thrombin, needs to be cleaved first in order to be active). In some embodiments, a protected thrombin comprises a protecting group (e.g., peptide mimetic sequence that blocks the active site, a coat of PEG polymers, etc.). In some embodiments, the therapeutic moiety is Factor-X-shielded thrombin. In some embodiments, the Factor-X-shielded thrombin is displayed on the exterior of TF-targetted nanofibers. In some embodiments, the thrombin is rendered inactive by the shielding effect of the Factor X protecting moiety. In some embodiments, upon delivery to a site of active hemorrhage, Factor X is converted to Factor Xa by Factor IXa or the factor VIIa/TF complex, thereby un-shielding thrombin and exposing active thrombin to the site of active hemorrhage. In such embodiments, the thrombin is unable to exert its clotting cascade effects until delivery to the site of active hemorrhage.

In some embodiments, additional therapeutic moieties find use in embodiments herein, either in addition to the procoagulants described above (e.g., nanofibers displaying two or more therapeutics) or as stand-alone therapeutic moieties. In other embodiments, the TF-targeted nanofibers described herein may be co-administered with other therapeutics (e.g., for the treatment of hemorrhage or other conditions/injuries associated therewith). Examples of therapeutic moieties and agents for inclusion in/on the nanofibers herein and/or for co-administration with the nanofibers herein include anesthetics, antibiotics (antimicrobials), anti-inflammatory agents, procoagulant agents, fibrosis-inhibiting agents, anti-scarring agents, leukotriene inhibitors/antagonists, cell growth inhibitors and the like.

Examples of non-steroidal anti-inflammatories include, but are not limited to, naproxen, ketoprofen, ibuprofen as well as diclofenac; celecoxib; sulindac; diflunisal; piroxicam; indomethacin; etodolac; meloxicam; r-flurbiprofen; mefenamic; nabumetone; tolmetin, and sodium salts of each of the foregoing; ketorolac bromethamine; ketorolac bromethamine tromethamine; choline magnesium trisalicylate; rofecoxib; valdecoxib; lumiracoxib; etoricoxib; aspirin; salicylic acid and its sodium salt; salicylate esters of alpha, beta, gamma-tocopherols and tocotrienols (and all their d, l, and racemic isomers); and the methyl, ethyl, propyl, isopropyl, n-butyl, sec-butyl, t-butyl, esters of acetylsalicylic acid.

Examples of anesthetics include, but are not limited to, licodaine, bupivacaine, and mepivacaine. Further examples of analgesics, anesthetics and narcotics include, but are not limited to acetaminophen, clonidine, benzodiazepine, the benzodiazepine antagonist flumazenil, lidocaine, tramadol, carbamazepine, meperidine, zaleplon, trimipramine maleate, buprenorphine, nalbuphine, pentazocain, fentanyl, propoxyphene, hydromorphone, methadone, morphine, levorphanol, and hydrocodone. Local anesthetics have weak antibacterial properties and can play a dual role in the prevention of acute pain and infection.

Examples of antimicrobials include, but are not limited to, triclosan, chlorhexidine, rifampin, minocycline (or other tetracycline derivatives), vancomycin, gentamycine, cephalosporins and the like. Further antimicrobials include aztreonam; cefotetan and its disodium salt; loracarbef; cefoxitin and its sodium salt; cefazolin and its sodium salt; cefaclor; ceftibuten and its sodium salt; ceftizoxime; ceftizoxime sodium salt; cefoperazone and its sodium salt; cefuroxime and its sodium salt; cefuroxime axetil; cefprozil; ceftazidime; cefotaxime and its sodium salt; cefadroxil; ceftazidime and its sodium salt; cephalexin; cefamandole nafate; cefepime and its hydrochloride, sulfate, and phosphate salt; cefdinir and its sodium salt; ceftriaxone and its sodium salt; cefixime and its sodium salt; cefpodoxime proxetil; meropenem and its sodium salt; imipenem and its sodium salt; cilastatin and its sodium salt; azithromycin; clarithromycin; dirithromycin; erythromycin and hydrochloride, sulfate, or phosphate salts ethylsuccinate, and stearate forms thereof, clindamycin; clindamycin hydrochloride, sulfate, or phosphate salt; lincomycin and hydrochloride, sulfate, or phosphate salt thereof, tobramycin and its hydrochloride, sulfate, or phosphate salt; streptomycin and its hydrochloride, sulfate, or phosphate salt; vancomycin and its hydrochloride, sulfate, or phosphate salt; neomycin and its hydrochloride, sulfate, or phosphate salt; acetyl sulfisoxazole; colistimethate and its sodium salt; quinupristin; dalfopristin; amoxicillin; ampicillin and its sodium salt; clavulanic acid and its sodium or potassium salt; penicillin G; penicillin G benzathine, or procaine salt; penicillin G sodium or potassium salt; carbenicillin and its disodium or indanyl disodium salt; piperacillin and its sodium salt; ticarcillin and its disodium salt; sulbactam and its sodium salt; moxifloxacin; ciprofloxacin; ofloxacin; levofloxacins; norfloxacin; gatifloxacin; trovafloxacin mesylate; alatrofloxacin mesylate; trimethoprim; sulfamethoxazole; demeclocycline and its hydrochloride, sulfate, or phosphate salt; doxycycline and its hydrochloride, sulfate, or phosphate salt; minocycline and its hydrochloride, sulfate, or phosphate salt; tetracycline and its hydrochloride, sulfate, or phosphate salt; oxytetracycline and its hydrochloride, sulfate, or phosphate salt; chlortetracycline and its hydrochloride, sulfate, or phosphate salt; metronidazole; dapsone; atovaquone; rifabutin; linezolide; polymyxin B and its hydrochloride, sulfate, or phosphate salt; sulfacetamide and its sodium salt; and clarithromycin.

Other therapeutic moieties/agents for use on or with the nanofibers herein include, but are not limited to, keflex, acyclovir, cephradine, malphalen, procaine, ephedrine, adriamycin, daunomycin, plumbagin, atropine, quinine, digoxin, quinidine, biologically active peptides, cephradine, cephalothin, cis-hydroxy-L-proline, melphalan, penicillin V, aspirin, nicotinic acid, chemodeoxycholic acid, chlorambucil, paclitaxel, sirolimus, cyclosporins, 5-fluorouracil and the like.

In some embodiments, provided herein are methods of treating and/or preventing hemorrhage in a subject comprising administering the TF-targeted nanofibers described herein. In some embodiments, pharmaceutical compositions comprising TF-targeted nanofibers are provided. Such pharmaceutical compositions may be formulated for any suitable route of administration (e.g., oral, topical, inhalation, intravenous, transdermal, etc.). Embodiments herein are not limited by the route of administration. In some embodiments, the appropriate route of administration is selected based upon the particular indication, or the location of the site of injury. Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In some embodiments, the TF-targeted nanofibers described herein are provided in kits for use in the treatment of acute injuries (e.g., injuries that may result in hemorrhagic bleeding). In some embodiments, a kit comprises elements useful for the deployment of TF-targeted nanofibers in the field (e.g., outside of a medical clinic, hospital, or other controlled setting). In some embodiments, a kit is utilized by military, medical, police, paramedic, or other users to treat or prevent hemorrhage in a field setting. In some embodiments, components of a kit include appropriate storage of the TF-targeted nanofibers (e.g., temperature control, container, etc.), appropriate delivery of the TF-targeted nanofibers (e.g., hypodermic needle, etc.), instructions for delivery of TF-targeted nanofibers, other devices and agents for the treatment of injuries (e.g., bandages, wound dressings, gauze, wipes, swabs, cleaning solutions, pain relievers, suturing kit, antibiotics, antiseptics, water, soap, etc.), etc.

EXPERIMENTAL

Example 1

Materials and Methods

PA Synthesis

TF-targeted peptides and PA for each sequence were synthesized using standard 9-fluorenyl methoxycarbonyl (Fmoc) solid-phase peptide synthesis (SPPS) on low-loading Rink amide 4-methylbenzhydrylamine resin (Millipore, Billerica, Mass.). For PA synthesis, the resin (0.25 mmol) was first loaded with Fmoc-Lys(4-methyltrityl) (1 mmol) using 2-(1H-benzotriazol-1-yl)-1,1,3,3-tetramethyluronium hexafluorophosphate (HBTU, 0.95 mmol) in dimethylformamide (DMF, 20 mL) for 4 hours by constant mixing in a peptide synthesis vessel. The 4-methyltrityl protecting group was then cleaved using a 4:5:91 mixture of trifluoroacetic acid (TFA):triisopropylsilane (TIPS):dichloromethane (DCM, 20 mL). Lauric acid ($C_{12}O_2H$)) was coupled to the deprotected ε-amine using the same coupling reagents, time, and equivalency as the Fmoc-amino acids. Fmoc was deprotected using a 30% piperidine solution in DMF for 20 minutes and resin was subsequently washed with DCM and DMF. The resin was then added to the Liberty Blue automated microwave peptide synthesizer (CEM, Matthews, N.C.) to finish the PA sequence. Afterwards, the resin was cleaved using a 95:5 TFA:TIPS cocktail for 2 hours.

Crude peptides and PAs were purified by reverse-phase high-performance liquid chromatography (HPLC) in a water-acetonitrile gradient, each containing 0.1% v/v TFA, by the Peptide Synthesis Core Facility in the Simpson Querrey Institute (SQI) at Northwestern University (ref. 15; herein incorporated by reference in its entirety). The filler Cys-PA CKKAAVV(K)-$C_{12}$ (SEQ ID NO: 11) was fluorescently labeled by reacting AlexaFluor 546-$C_5$-maleimide (1 mmol, Life Technologies, Grand Island, N.Y.) with an excess of the Cys-PA (4 mmol) in HEPES buffer at pH 7.4. Crude reaction was lyophilized and purified using HPLC to separate excess unreacted PA. PAs were then co-assembled at different percentages with the non-targeted ($K_2A_2V_2$ PA filler) KKAAVV(K)-$C_{12}$ PA (SEQ ID NO: 5) and the Alexa-CKKAAVV(K)-$C_{12}$ PA (1%) (SEQ ID NO: 11) by dissolving them in hexafluroisopropanol (HFIP), and mixing them together for 15 minutes. Samples were frozen in liquid $N_2$ and HFIP was removed in vacuo. Samples were then re-dissolved in distilled deionized water, and lyophilized. Co-assembly ratios for experiments comparing the different TF-PA and non-specific PA were 25% targeted PA to 75% non-targeted PA ($K_2A_2V_2$ filler PA), with 1% of the non-targeted PA fluorescently tagged. Co-assembly ratios for experiments comparing ligand density of the RTL PA were 10%, 25%, 50%, 75%, and 100%, all of which contained 1% fluorescently labeled PA (non-targeted).

PA Characterization

Images for cryo-TEM were obtained using a Hitachi HT-7700 Biological TEM (Hitachi High Technologies America, Schaumburg, Ill.) equipped with a LaB6 filament working at an accelerating voltage of 100 kV. PA samples were plunge frozen using a Vitrobot Mark IV (FEI, Hillsboro, Oreg.) operating at 25° C. with 100% humidity. The PA sample (8 μL) was deposited on 300 square mesh copper grids with a lacey carbon film (Ted Pella, Redding, Calif.), blotted, and plunged into a liquid ethane reservoir cooled by liquid nitrogen. Following vitrification, the sample was transferred to a Gatan 626 cryo-holder (Gatan, Pleasanton, Calif.) under liquid nitrogen with the aid of a transfer stage. Images were acquired using an Onus SC 1000A CCD camera. All PA formulations were imaged at concentrations of 0.5 mg/mL in Hank's Balanced Salt Solution (HBSS). Diameter of the nanofibers was measured using ImageJ software (NIH, Bethesda, Md.).

CD measurements were performed at a concentration of 0.2 mg/mL in HBSS using a Jasco J-815 CD spectrophotometer (Jasco Analytic Instruments, Easton, Md.) at 25° C. using a 0.01 mm path length demountable quartz cuvette.

In Vitro Binding Assay

A plate-based binding assay for the TF-targeting peptides was performed as follows. Peptides were dissolved in water at a concentration of 60 μM and coated onto BD Falcon OptiLux 96-well plates (BD Biosciences, Franklin Lakes, N.J.) by incubating them at 37° C. for 2 hours, then at 4° C. overnight. Next, wells were blocked using Superblock phosphate buffered saline (PBS) blocking buffer (200 μL per well, Thermo Scientific, Waltham, Mass.) for 2 hours at room temperature, then washed two times with water. Rat recombinant TF (Cloud Clone Corp, Houston, Tex.) was added in amounts of 12.5-75.0 ng, dissolved in PBS for a total volume of 50 μL/well and incubated at room temperature for 4 hours. Plates were rinsed with water twice, then blocked with Superblock PBS blocking buffer for 30 minutes at room temperature. Colorimetric immunodetection was then performed by incubating wells with anti-TF antibody (Cat. #: ab104513, rabbit polyclonal, Abcam, Cambridge, Mass.) dissolved in Superblock PBS blocking buffer (1:5000) at 4° C. overnight. Wells were washed in water 4 times, and then incubated with a secondary goat-anti-rabbit antibody (Thermo scientific, Rockford, Ill.) conjugated to horseradish peroxidase and dissolved 1:5000 in Superblock PBS blocking buffer for 2 hours at room temperature. Wells were then rinsed 4 times in water, developed using TMB developing solution (TMB Substrate, Thermo Scientific, Waltham, Mass.) for 15 minutes, then stopped with 0.18 M $H_2SO_4$ (Sigma Aldrich, St. Louis, Mo.). Plates were immediately read using an Epoch plate reader (BioTek, Winooski, Vt.) at 450 nm. Wells were coated in triplicate, and the assay was performed three times. Treatment groups were each peptide as stated above. Negative controls were wells coated with blocking buffer rather than peptide, and positive controls were wells coated with rat recombinant TF (Cloud Clone Corp) at 12.5 and 25 ng/well.

Animal Model

Adult male Sprague Dawley rats weighing 350-450 g were anesthetized using inhaled isoflurane (1-5%). They underwent invasive hemodynamic monitoring via common carotid artery cannulation (ref 27; herein incorporated by reference in its entirety). PA solutions were prepared for each binding sequence by dissolving 2.5 mg PA in 0.5 mL HBSS for a final concentration of 5 mg/mL. Animals were then prepped and draped in a sterile manner to undergo the liver punch hemorrhage model. A midline laparotomy was performed and the left lateral lobe of the liver was exposed. The animal then received tail vein injection with the PA solution (500 μL). This dose was chosen based on prior work demonstrating that this dose was well tolerated by the rat and resulted in surface binding of the targeted nanofiber to its target sequence (refs. 14, 26; herein incorporated by reference in their entireties). Immediately after injection, a 12-mm punch was created in the left lateral lobe of the liver to induce hemorrhage. The liver was allowed to bleed freely into the intra-abdominal cavity. Blood loss was collected on pre-weighed gauze and hemodynamics were recorded at 2-5 minute intervals for a total of 30 minutes (FIG. 9, Panel D). At the end of 30 minutes, animals were euthanized.

Tissue Processing

In situ perfusion with 400 mL of a PBS solution was performed, and organs including the kidneys, spleen, lung, uninjured liver, and injured lobe of the liver were collected for tissue processing. Samples were fixed in 2% paraformaldehyde for 2 hours, then 30% sucrose overnight. Samples were then frozen in Tissue-Tek OTC compound (Sakura Finetek, Torrance, Calif.) over liquid nitrogen and stored at −20° C. A LEICA CM 1950 cryostat (LEICA Biosystems, Buffalo Grove, Ill.) was used to cut samples into 10-μm sections, which were stained with 4',6-diamidino-2-phenylindole (DAPI, Invitrogen, Grand Island, N.Y.), and fixed with ProLong® Gold antifade reagent (Life Technologies, Eugene, Oreg.). For evaluation of inflammation, histological slides of uninjured liver and the injured lobe of the liver from rats treated with RTL PA nanofiber were incubated with an anti-ED1 antibody (Cat # MCA341R, ABD Serotec, Hercules, Calif.) at a 1:1000 dilution, or an anti-MPO antibody (Cat # av9535, Abcam, Cambridge, Mass.) at a 1:100 dilution in IHC-Tek antibody diluent (IHC World, Woodstock, Md., USA) for 1 hour at room temperature. After a 2 minute rinse of PBS, the sections for ED1 staining were incubated with a goat anti-rabbit IgG (Alexa-Fluor 647, Cat # A-21424, Invitrogen, Waltham, Mass.) 1:100. For MPO staining, sections were incubated with goat anti-mouse IgG (H+L) secondary antibody (AlexaFluor 647 conjugate, Cat # A-11007, Invitrogen, Waltham, Mass.) at 1:100. Both secondary antibodies were incubated for 1 hour at room temperature. Nuclei were stained with DAPI 1:500 in PBS for 1 minute (Cat # D3571, Thermo Fisher Scientific, Waltham, Mass.). Finally, slides were coverslipped with ProLong Gold (Cat # P36930, Thermo Fisher Scientific, Waltham, Mass.).

Fluorescent Microscopy

Digital images were acquired using a Zeiss LSM-510 microscope (Hallbergmoos, Germany) with a 20× objective. The HE CY3 filter (Zeiss filter #43) using excitation and emission wavelength 550-575 nm and 605-670 nm, respectively, was used to assess PA fluorescence. The DAPI filter (Zeiss filter #49) using excitation and emission wavelength 365-395 nm and 445-450 nm, respectively, was used for nuclear staining. The green fluorescent protein filter (Zeiss filter #38) using excitation and emission wavelengths of 470-495 nm and 525-550 nm, respectively, was used to assess tissue auto-fluorescence.

Ex Vivo Blood Studies

To assess the hemolytic capacity of the RTL PA nanofiber, fresh rat blood was collected into citrate-containing tubes and centrifuged at 1,000×g for 10 minutes. The RBC pellet was resuspended with HEPES-saline-gelatin-EDTA buffer and incubated for 10 minutes at 37° C., washed again with HEPES-saline-gelatin-EDTA buffer once, and then washed with HEPES-saline-gelatin-metal buffer twice. Washed RBC were incubated with 100 μM RTL PA and 400 RTL PA for 5, 20, and 60 minutes at 37° C. in 1.5 mL Eppendorf tubes. Samples were centrifuged at 1000×g for 10 minutes at 4° C. and the supernatant was transferred into 96-well plate to measure absorbance at 412 nm to detect presence of hemoglobin.

To assess platelet adhesion to the RTL PA nanofiber, rat platelet rich plasma (PRP) and platelet poor plasma (PPP) were prepared from fresh rat blood by centrifugation at 150×g for 15 minutes and 840×g for 20 minutes, respectively, at room temperature. PRP was diluted with PPP to a final platelet concentration of $2 \times 10^8$/mL. A 96-well plate was coated with RTL PA (1 mg/mL) at 37° C. overnight. Small (0.2×0.2 inch) plastic pieces were cut from a 10-cm cell culture dish. Plastic pieces were coated with RTL PA (1 mg/mL) PA in HEPES buffer (25 mM) at 37° C. overnight. Diluted platelets ($4 \times 10^7$ platelets) were incubated with both coated and uncoated plastic pieces at 37° C. for 15 minutes. Samples were fixed in 4% fresh paraformaldehyde, and dehydrated in a series of EtOH washes. Samples were then critically point dried, mounted, and coated with 5 nm of osmium before imaging using a LEO Gemini 1525 sFEG SEM.

To measure free fibrinogen levels in whole blood, freshly collected whole blood was centrifuged, and to the plasma fraction RTL PA (80 μM) was added. Free fibrinogen levels were measured in control and RTL PA-treated samples by IDEXX.

LC-MS Stability Study

To assess the stability of the RTL PA nanofiber over time, the RTL PA nanofiber (50 μM) was incubated in rat plasma at 37° C. for 0, 5, 10, 15, 30, 60, 120, and 180 minutes. At the end of the incubation time, tris(2-carboxyethyl)phosphine (TCEP, 5 mM final) was added and the sample was treated with 0.1% formic acid in acetonitrile (ACN/0.1% formic acid) (2:1) to precipitate out protein. After centrifugation at 10,000 rpm for 10 minutes, the supernatant was transferred to a 96-well plate and dried under nitrogen. Samples in 96-well plate were resuspended within the LC aqueous fluent (0.1% formic acid in $H_2O$) and placed for automatic injection into an Agilent 6510 Quadrupole Time-of-Flight (Q-TOF) LC-MS (mass spectrometry) system. In MS mode, a total ion chromatogram was obtained through an LC run that consisted of a 5% to 95% ACN/0.1% formic acid gradient over 30 minutes using a Phenomenex Jupiter C18 analytical column. Using the Mass Hunter Agilent software, extracted ion chromatograms of the ions of the +4 charge state of RTL PA were integrated to create a calibration curve and quantify the amount of PA at each time point.

Statistics

Blood loss was presented as % total blood volume. Results were expressed as mean+/−the standard error of the mean. SigmaPlot (Systat Software, Inc. San Jose, Calif.) was used to determine differences between groups using one way analysis of variance (ANOVA) with the Duncan's post hoc method for all pairwise multiple comparisons. To analyze the effect of treatment over time for blood loss and MAP, a linear mixed effect regression model with time and treatment group as fixed effects, and time points nested within each rat subject (i.e., repeated measures) was used. Data were log transformed for analysis. The fixed effects were estimated and a 95% confidence interval used to determine differences between the treatment groups. The model was fit using PROC MIXED on SAS (SAS Institute Inc., Cary, N.C.).

Example 2

Targeted PAs Form Nanofibers and Display Increased β-Sheet Character, which Increases with Ligand Density TF binding peptides were selected by examining the interaction between TF and Factor VII (FVII). Studies on the crystal structure of TF and FVII, as well as mutational studies, have identified several areas important for binding (refs 9, 17-18; herein incorporated by reference in their entireties). Three linear binding sequences were selected initially from FVII. The first sequence is from the EGF-2 domain and contains arginine 79, which has been shown to be important for TF binding by crystal structure interactions and through mutational studies refs. 17-19; herein incorporated by reference in their entireties). This sequence (SEQ ID NO:1; EGRNCETHKDDQL), is referred to as the EGR sequence (FIG. 1, Panel A). The next sequence is located on the heavy chain of FVII, forms an alpha helix, and contains the amino acids methionine 306 and aspartate 309, both of which have been shown to be important in the binding of FVII to TF (refs. 18-19; herein incorporated by reference in their entireties). This sequence, (SEQ ID NO: 2; RLMTQDCLQQRSK) is referred to as the RLM sequence (FIG. 1, Panel B). The third sequence is also located on the heavy chain of FVII, forms an alpha helix, and contains arginine 277, which has been found to be important in the binding of FVII to TF (refs. 18-19; herein incorporated by reference in their entireties). This sequence (SEQ ID NO: 3; RTLAFVRFK) is referred to as the RTL sequence (FIG. 1, Panel C). In addition, a non-specific peptide, consisting of the filler peptide $A_2V_2K_2$—$C_{12}$, was selected as a non-targeted control.

Figure 2A:
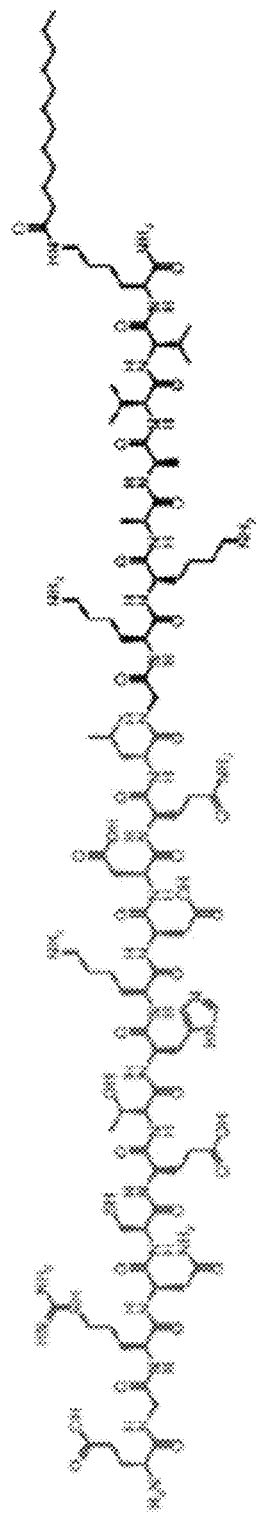
FIGS. 2A-H. Targeted PAs form nanofibers and display increased β-sheet character, which increases with ligand density. Chemical structures of the (FIG. 2A) EGR PA, (FIG. 2B) RLM PA, and (FIG. 2C) RTL PA. Cryo-transmission electron microscopy of the (FIG. 2D) EGR PA, (FIG. 2E) RLM PA, and (FIG. 2F) RTL PA nanofibers confirms the fiber shape. Circular dichroism demonstrates (FIG. 2G) increased β-sheet formation with the EGR PA, RLM PA, and RTL PA nanofibers as compared to the nontargeted nanofibers (K2A2V2 PA filler), and (FIG. 2H) increased β-sheet formation with increasing RTL targeting ligand density.
Figure 2B:
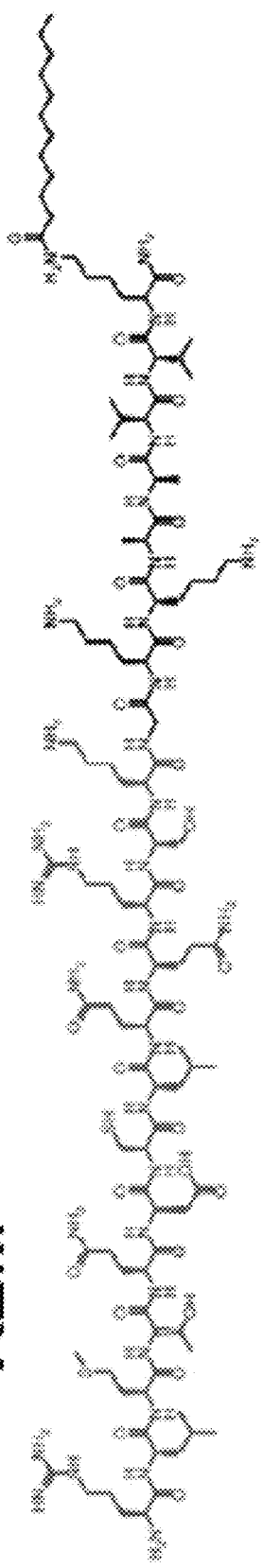
Figure 2C:
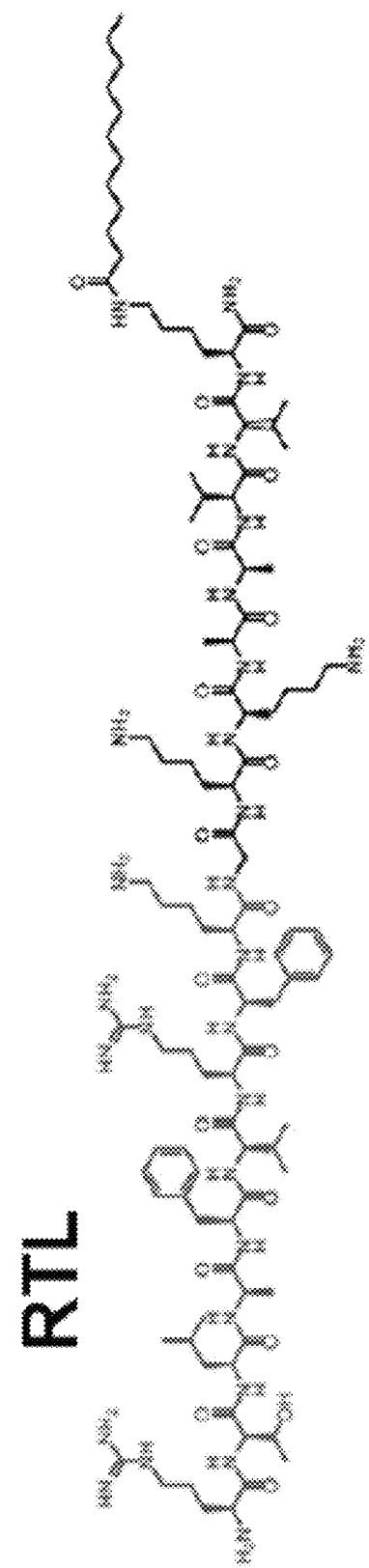
Figure 2D:
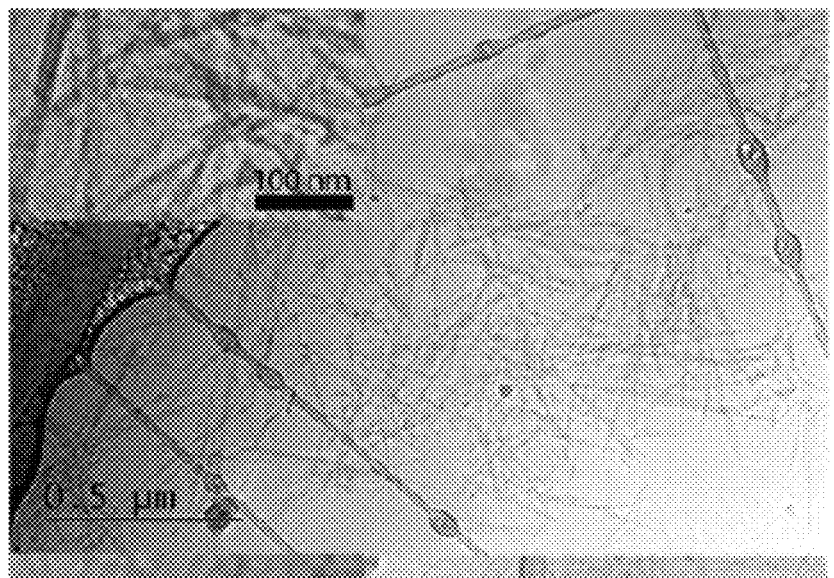
Figure 2E:
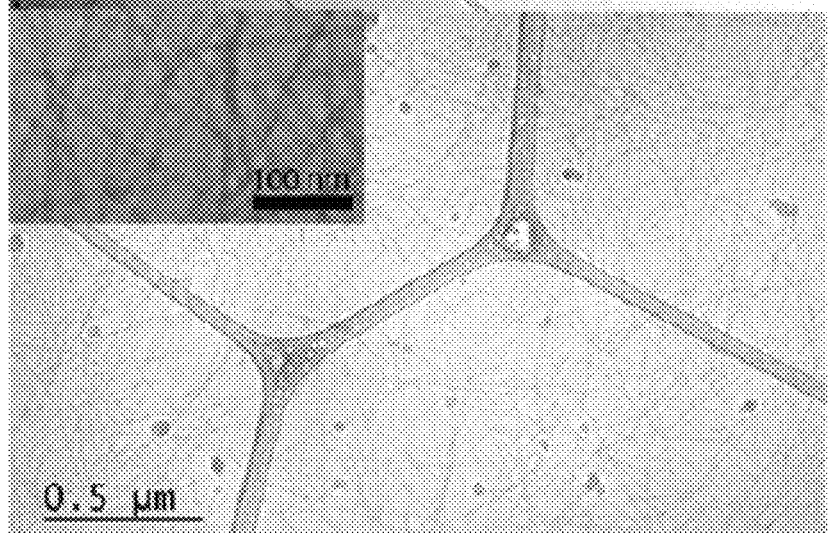
Figure 2F:
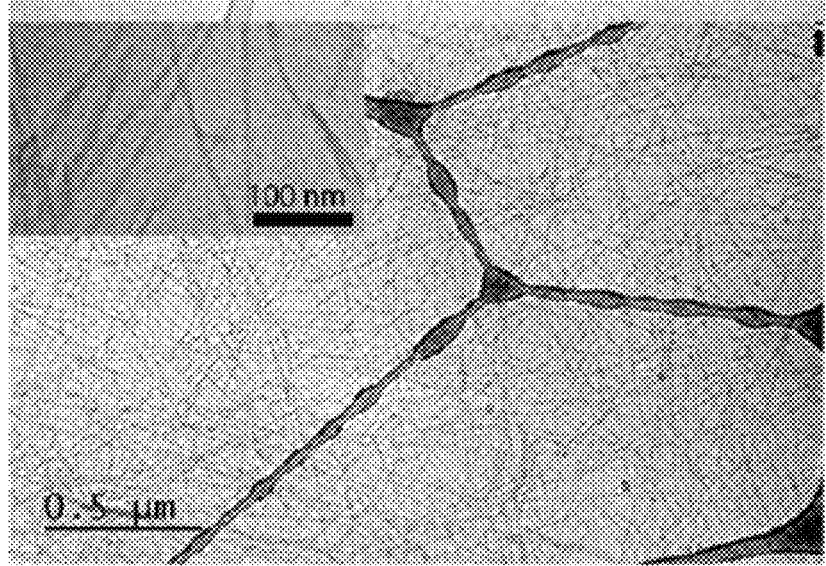
Figure 2G:
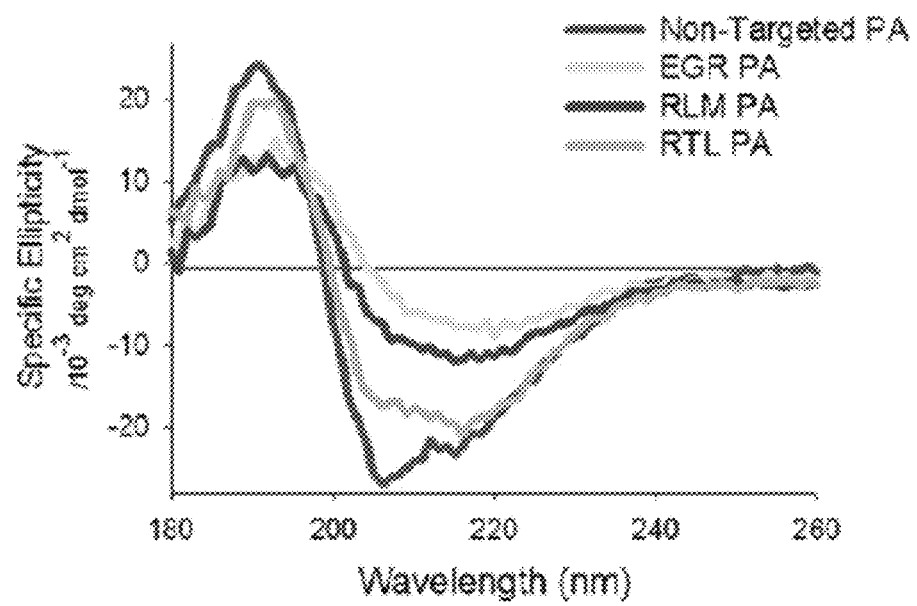
Figure 2H:
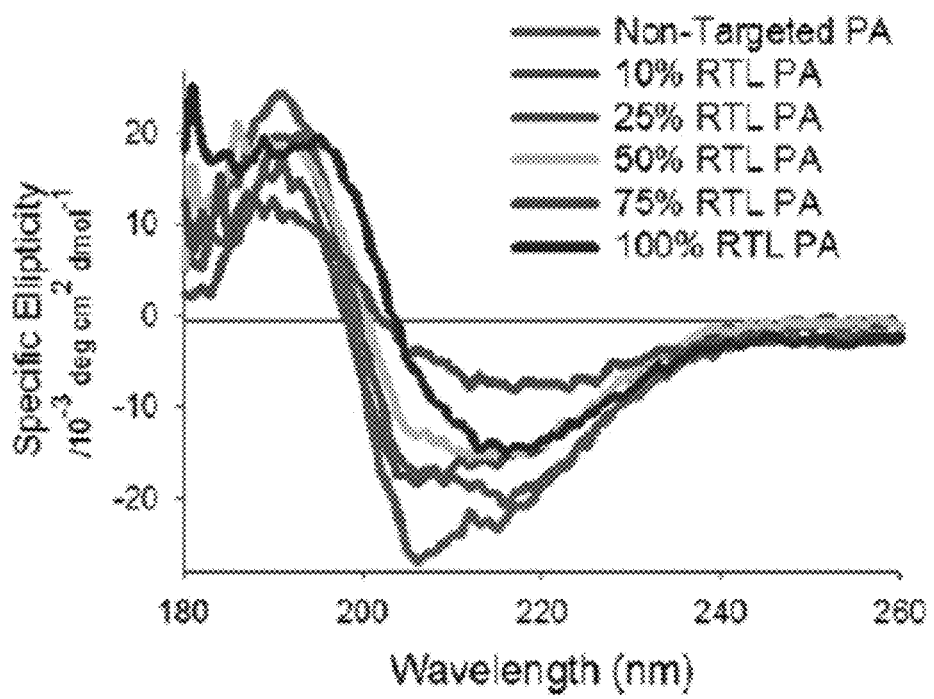

Each of the three targeted nanofibers (EGR, RLM, and RTL, FIG. 2A-C) was synthesized and co-assembled in a ratio of 25% targeted PA (EGR PA, RLM PA and RTL PA) to 75% non-targeted PA ($K_2A_2V_2$ PA filler). For RTL, this range was further expanded to include 10% to 100% RTL PA. Cryo-transmission electron microscopy (Cryo-TEM) confirmed fiber formation (FIG. 2D-F) and found that the fibers were between 10 and 19 nm in diameter (Figure S1) with lengths in the micrometer range. For the RTL targeted PA, as the percentage of the RTL targeting peptide increased, the fibers increased in average diameter from 11±2 nm to 16±3 nm (Figure S1). In addition, shorter assemblies appeared (400-900 nm in length) displaying ribbon-like character. Higher targeting epitope densities potentially favor epitope-epitope interactions that could affect the overall supramolecular structure. Circular dichroism performed on each targeted and non-targeted nanofiber showed that the targeted nanofibers had increased β-sheet character over the non-targeted nanofiber (FIG. 2G). In addition, increasing the percent of the targeting ligand increased the β-sheet character compared to the non-targeted nanofibers, as evidenced by the blue-shift of the circular dichroism (CD) minima closer to 220 nm (FIG. 2H).

Example 3

RLM and RTL TF-Targeting Peptides Bind to Recombinant TF In Vitro

To determine which of the three binding peptide sequences bind TF the best, a binding assay was performed. Both the RLM and RTL peptide sequences had the highest absorbance (0.29±0.02 and 0.28±0.03, respectively) compared with the negative control (0.18±0.02), non-specific peptide (0.2±0.03), and EGR peptide sequence (0.19±0.3, FIG. 3A). In addition, the RLM and RTL peptides were found to have absorbance readings similar to the recombinant TF-coated positive control group (0.32±0.01), indicating that the RLM and RTL peptides achieved maximal binding to recombinant TF. To further delineate the nature of the binding, a dose response assay was performed in which the RLM and RTL peptides were coated on 96-well plates and incubated with increasing concentrations of recombinant TF. Colorimetric immunodetection demonstrated increased absorbance with increasing concentrations of recombinant TF (FIG. 3B), further validating the binding of RLM and RTL to TF in vitro.

Example 4

TF-Targeted Nanofibers Bind to Areas of Liver Injury In Vivo

Figure 4A:
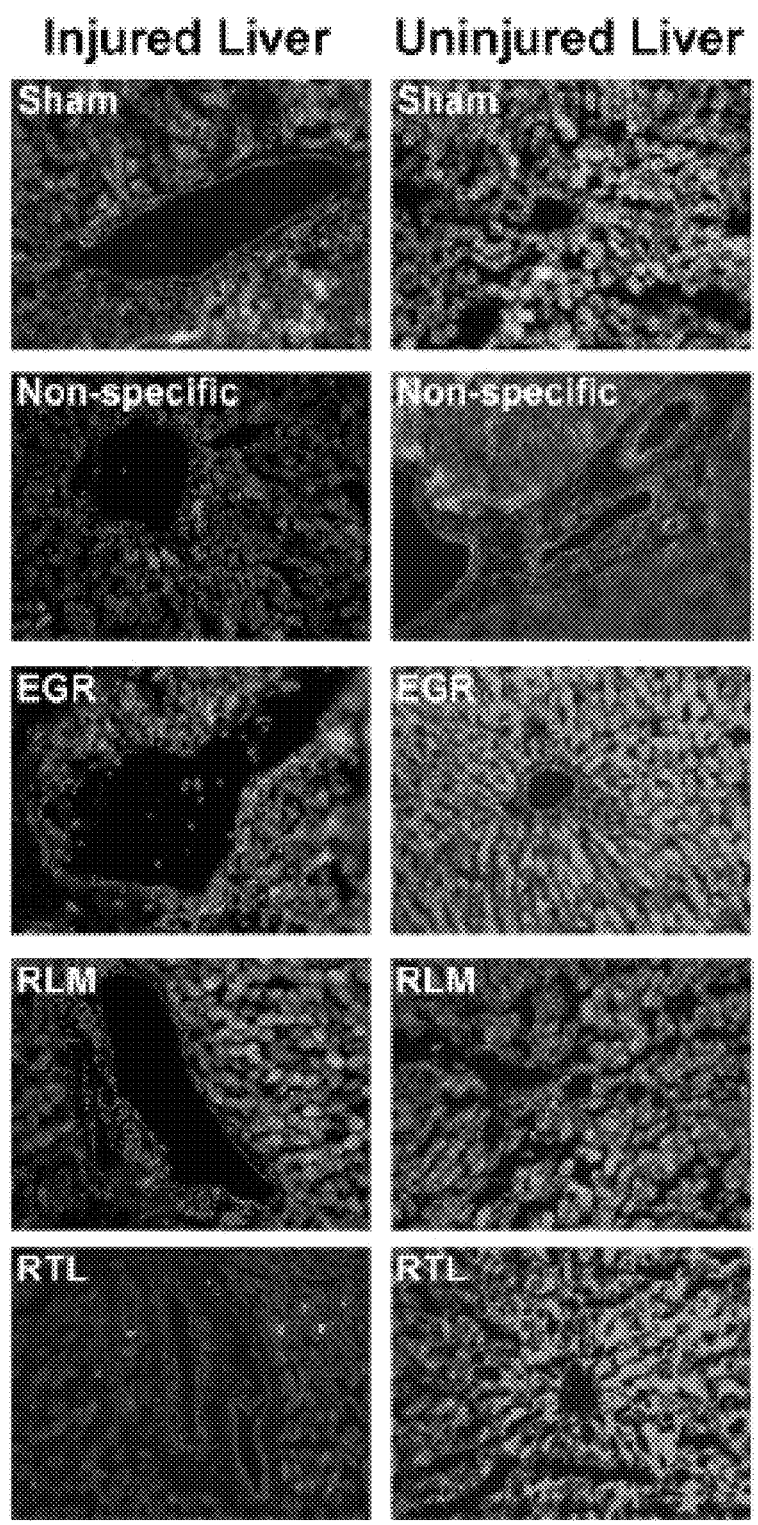

To determine if the targeted nanofibers bind to TF in vivo, rats underwent the liver punch injury model and binding of the different targeted nanofibers was assessed using fluorescent imaging of the liver. As can be seen in FIG. 4A, no fluorescence was observed in the injured liver from sham-treated rats or rats that received non-specific PA nanofibers (FIG. 4A). Fluorescence was observed near the vasculature in the injured liver from rats that received the EGR PA, RLM PA, and RTL PA targeted nanofibers (FIG. 4A), indicating binding of the targeted nanofibers to the site of injury. No fluorescence was observed in liver remote to the area of injury (i.e., the uninjured liver) in any of the treatment groups.

Example 5

RTL TF-Targeted Nanofibers Reduce Hemorrhage in a Rat Model of Liver Injury

Next, to determine if the targeted nanofibers impact hemorrhage, blood loss during the liver punch model was assessed for all treatment groups. Cumulative blood loss increased over time for sham treated animals. All three targeted nanofibers, as well as the non-specific PA nanofiber, had a time-dependent effect of reducing blood loss compared to the sham treated rats (*p<0.001, FIG. 4B). However, only the RTL PA targeted nanofiber reduced blood loss over time compared to both sham and non-specific PA nanofiber treated rats (⁺p<0.05, FIG. 4B). To assess the effect of treatment group independent of time, total blood loss was analyzed. The RTL PA nanofiber was the only sequence that significantly reduced total blood loss compared to sham treated rats (53% reduction, FIG. 4C). No statistically significant differences were noted in total blood loss between the other treatment groups and sham treated rats: non-specific PA (21±2%), EGR PA (19±3%), and RLM PA (21±1%).

Example 6

RTL TF-Targeted Nanofibers with Increasing Ligand Density Bind to Injured Liver

Figure 5:
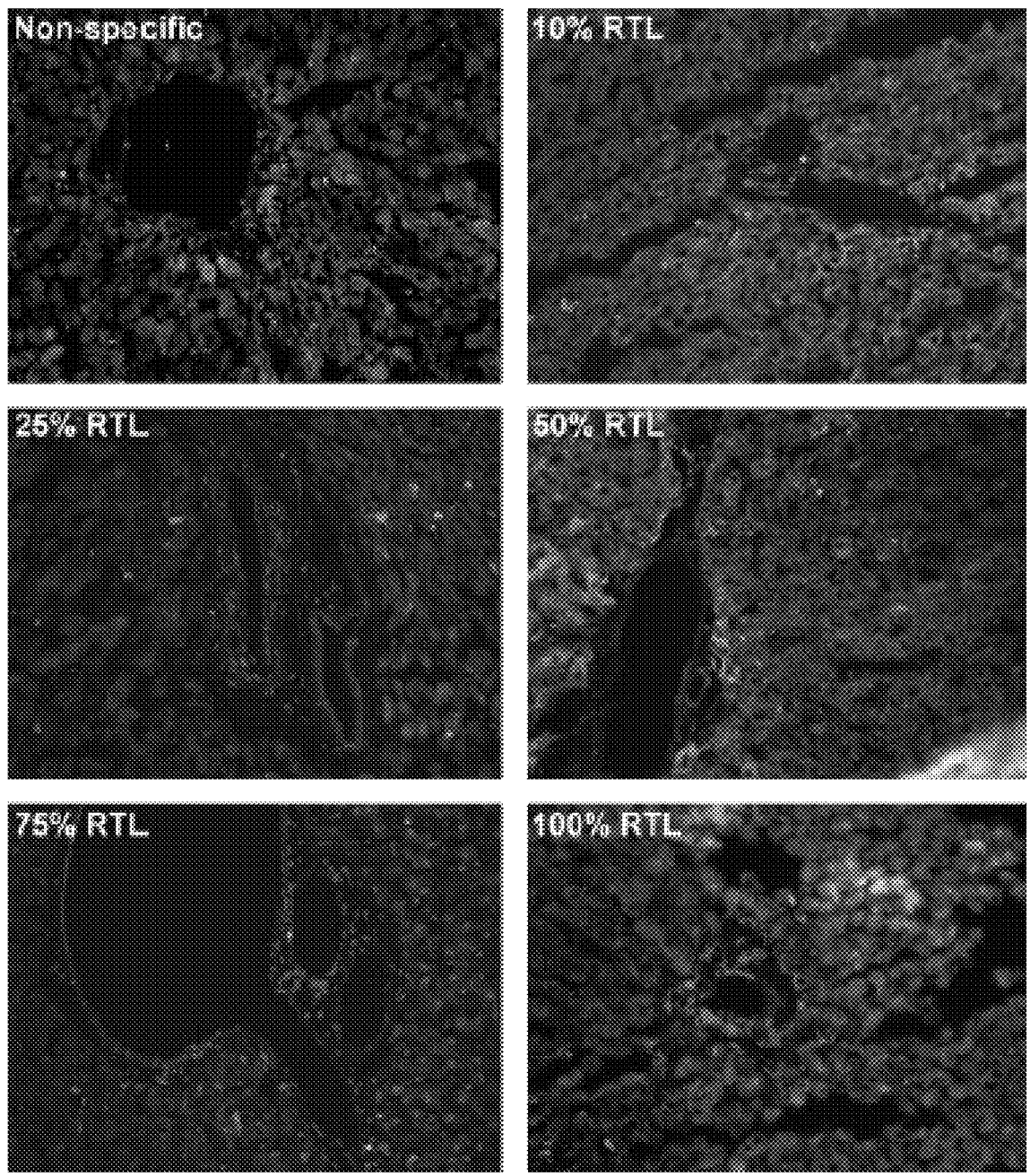
FIG. 5. Binding of RTL TF-targeted nanofiber with increasing ligand densities to injured liver. Fluorescent microscopy of the injured liver reveals no red fluorescence with the nonspecific PA nanofiber, suggesting no binding.

Since both the RLM and RTL binding sequences exhibited superior binding compared to the EGR sequence in the in vitro binding assay, but only the RTL PA targeted nanofiber exhibited less blood loss in the animal model of hemorrhage, the RTL PA was selected for further evaluation. The effect of targeting ligand density was evaluated on both binding and response to hemorrhage by co-assembling different ratios of the targeted PA (10-100%) with the non-targeted PA ($K_2A_2V_2$ PA filler). Similar to previous experiments, animals underwent tail vein injection of the nanofiber followed by immediate liver injury. Fluorescent microscopy of injured liver from rats that received the non-specific or RTL PA nanofiber with different targeting densities is shown in FIG. 5. No fluorescence was observed in the injured portion of the livers in animals that received the non-specific PA nanofiber. Fluorescent signal was noted in the injured portion of the livers in rats that received the RTL PA nanofiber, with clear localization near the vasculature. Of interest is that fluorescent signal was detected with all RTL PA nanofiber ligand densities evaluated and fluorescence qualitatively increased with increasing ligand density.

Example 7

Ability of RTL TF-Targeted Nanofiber to Prevent Blood Loss Increases as Ligand Density Increases Next, the impact of targeting ligand density on blood loss over time was assessed using the rat liver punch model.

Figure 6A:
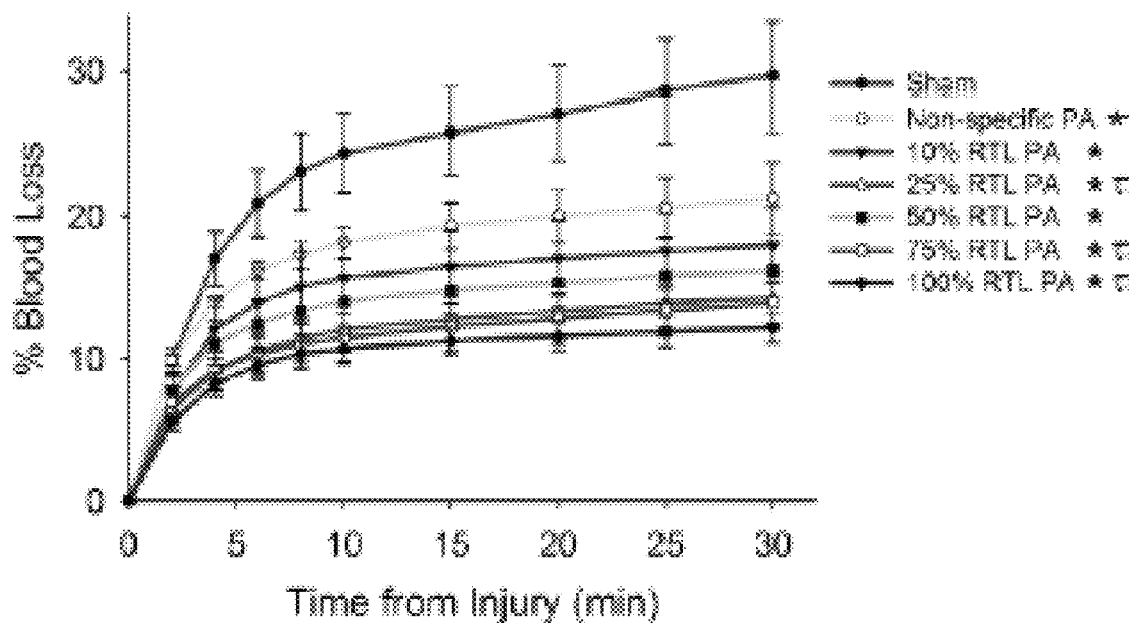
FIGS. 6A-C. Ability of RTL TF-targeted nanofiber to prevent blood loss increases as ligand density increases and mean arterial pressure was not affected by up to 75% RTL TF-targeted nanofiber.
Figure 6B:
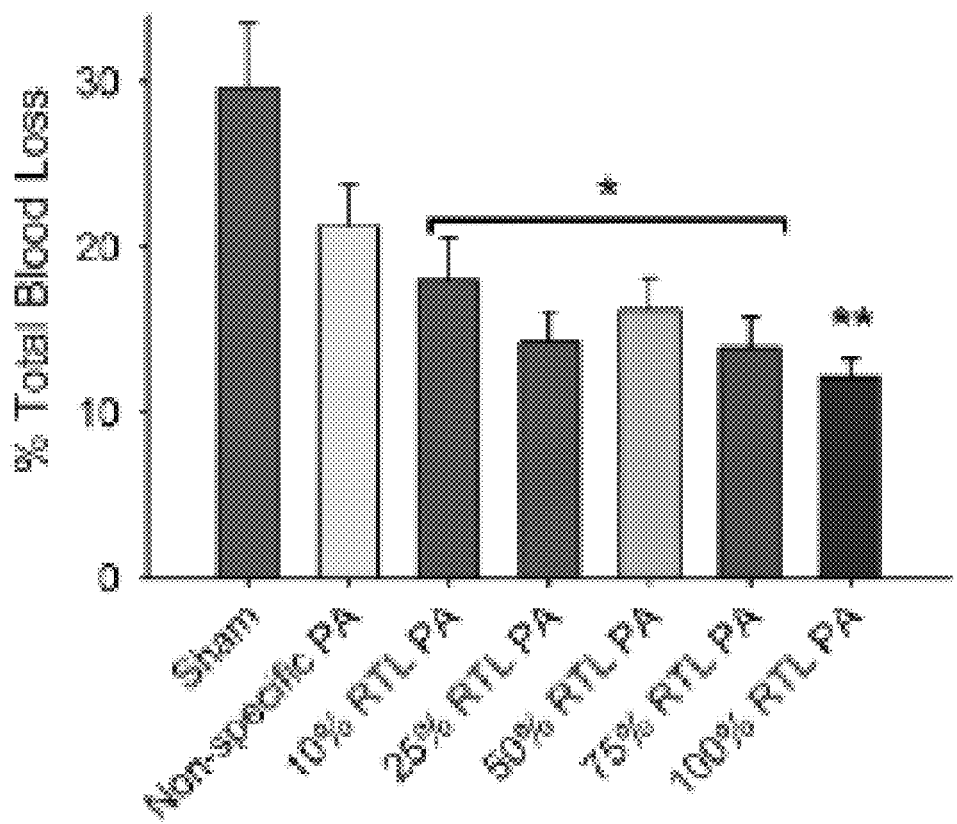

Compared to sham treated animals, as the RTL targeting ligand density was increased, blood loss over time was reduced (FIG. 6A). Blood loss over time from animals that received the 25%, 75%, and 100% RTL PA nanofibers was significantly less compared to blood loss over time from animals that received the non-specific PA nanofiber (*p<0.001). To assess the effect of RTL ligand density independently of time, we evaluated total blood loss (FIG. 6B). There was a significant ligand density-dependent reduction on total blood loss (p=0.0081). The 100% RTL PA nanofiber resulted in 60% less blood loss compared to sham treated animals (12±1 vs. 30±4%, respectively). The 100% RTL TF-targeted nanofiber also reduced blood loss compared to the animals treated with non-specific PA nanofiber (21±2%). Blood loss for the 75% RTL (14±2%), 50% RTL (16±2%), 25% RTL (14±2%), and 10% RTL (18±3%) were each reduced compared to sham.

Figure 7:
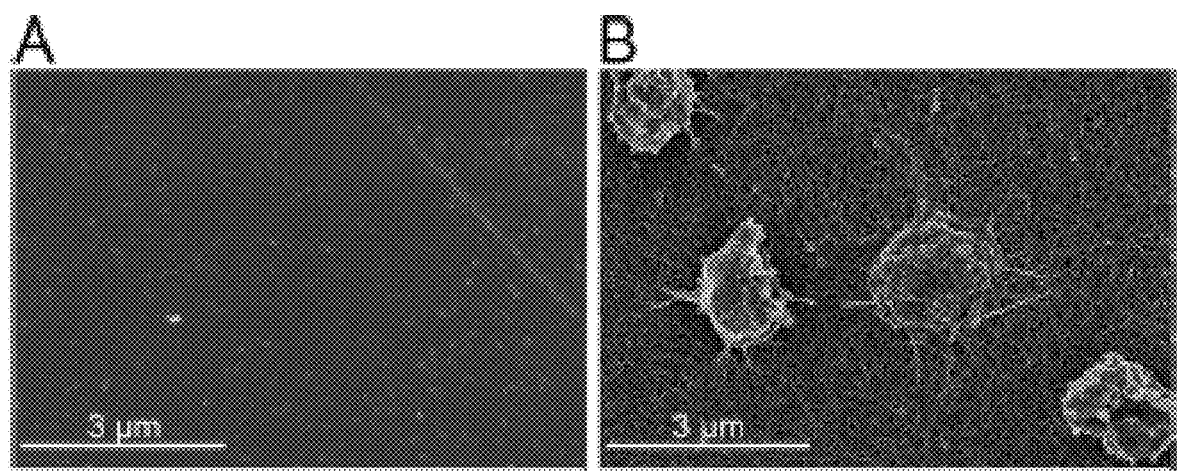
FIG. 7. Platelet adhesion to a RTL PA nanofiber-coated surface. (Panel A) SEM of untreated tissue culture plastic after incubation with platelets (4×10$^7$) for 15 min, followed by PBS wash. (Panel B) SEM of RTL PA nanofiber-coated tissue culture plastic after incubation with platelets (4×10$^7$) for 15 min, followed by PBS wash.

To assess the possible mechanism of action of the RTL PA nanofiber on reducing hemorrhage, platelet aggregation was evaluated and free fibrinogen levels were measured. First platelet adhesion to a RTL PA nanofiber network was analyzed using SEM. We found that platelets adhere to surfaces coated with RTL PA nanofiber whereas they do not adhere to uncoated tissue culture surfaces (FIG. 7). The effect of RTL PA on free fibrinogen levels in whole blood was also assessed. After collecting rat whole blood, plasma was incubated ex vivo with RTL PA (80 μM) or with saline. The free fibrinogen level in control plasma was 202±4 mg/dL, whereas in RTL PA nanofiber-treated plasma, it was below the limit of detection of the assay (<36 mg/dL), indicating that the RTL PA nanofiber bound to and consumed free fibrinogen.

Example 8

Biocompatibility and Safety of the RTL PA Nanofiber

Figure 6C:
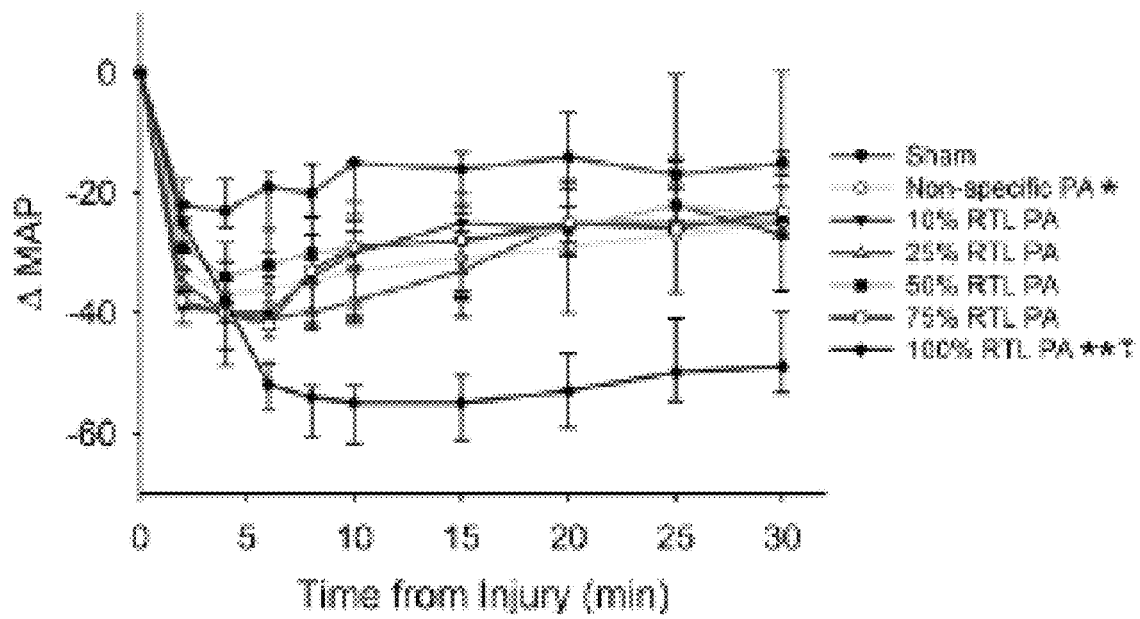

Mean arterial pressure (MAP) was assessed over time for all of the treatment groups (FIG. 6C). MAP change over time from animals that received 10%, 25%, 50%, and 75% RTL PA nanofibers was similar to sham and animals treated with non-specific PA nanofiber. However, the MAP change over time for animals that received the non-specific PA nanofiber was different from sham treated animals, and the MAP change over time for animals that received the 100% RTL PA was different from sham and 10%, 25%, 50%, and 75% RTL PA nanofiber treated animals.

Next the stability of the RTL PA nanofiber in rat plasma was assessed. It was found that there is a time-dependent decrease of RTL PA nanofiber. After 30 minutes, 70% of the RTL PA nanofiber is intact and present in plasma. After 2 hours, 44% of the RTL PA nanofiber remained (Figure S2).

To determine if the RTL PA nanofiber induced hemolysis, different concentrations of the RTL PA nanofiber were incubated with RBC and measured hemolysis. It was found that the RTL PA nanofiber at concentrations of 100 μM and 400 μM did not induce RBC hemolysis ex vivo. After 1 hour of incubation with $2.9 \times 10^{10}$ RBC, 100 μM of RTL PA nanofiber resulted in 1.4±0.1% hemolysis, 400 μM of RTL PA resulted in 2.0±0.1% hemolysis, whereas saline control resulted in 2.4±0.9% hemolysis.

The inflammatory response in the injured lobe of the liver was assessed in the presence and absence of RTL PA nanofiber by immunofluorescence. No difference was detected in the presence of myeloperoxidase (MPO)-positive cells (neutrophils), or ED1-positive cells (macrophages) between uninjured liver and injured liver from 25%, 75%, or 100% RTL PA nanofiber treated animals (Figure S3).

Example 9

Figure 8:
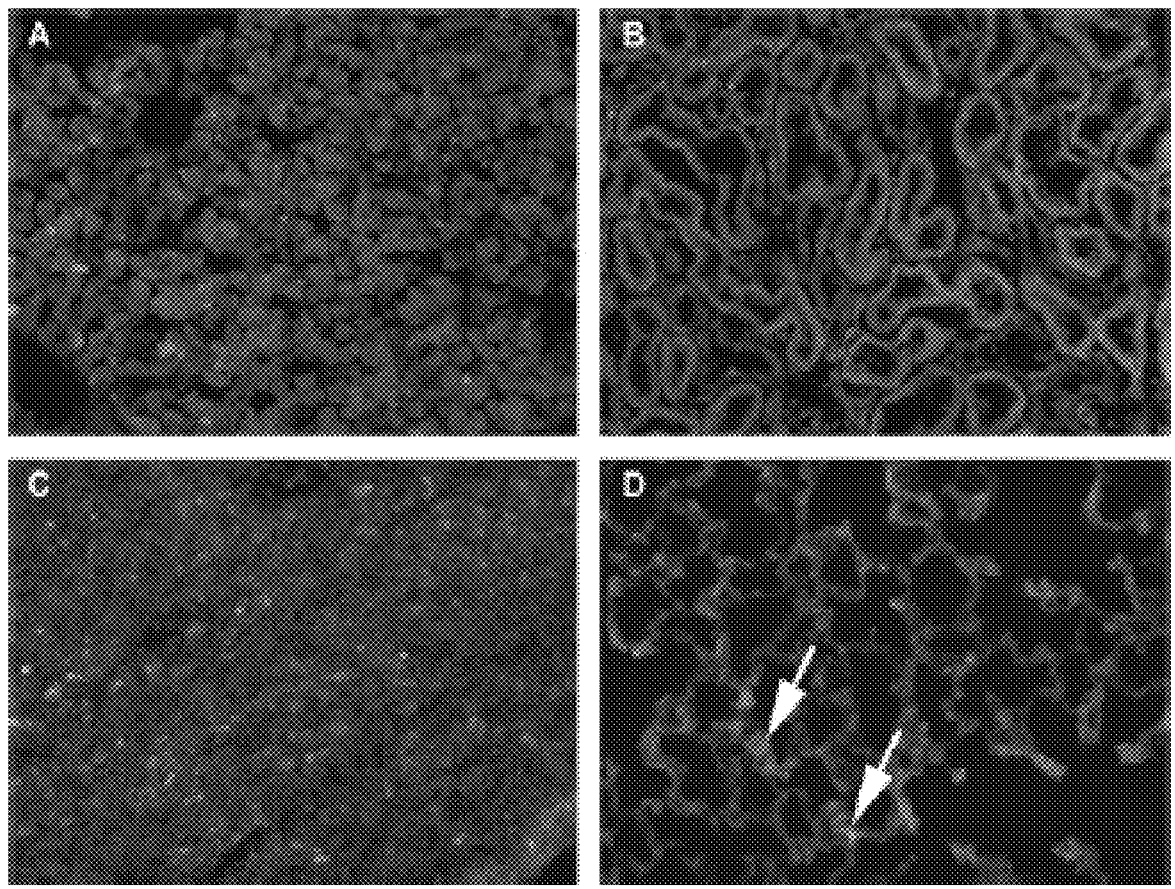
FIG. 8. RTL TF-targeted nanofiber does not bind to uninjured liver or other organs in vivo. Injection of the 75% RTL PA nanofiber into rats that underwent the liver punch injury model demonstrated no fluorescent signal in (Panel A) uninjured liver, (Panel B) kidney, and (Panel C) spleen. (Panel D) A very small amount of fluorescent signal was detected in the lung (arrows).

RTL TF-Targeted Nanofiber Does Not Bind to Uninjured Liver or Other Organs In Vivo To evaluate the biodistribution of the RTL PA nanofiber, and verify binding specificity, sections of uninjured liver, kidney, spleen, and lung from animals injected with the 75% RTL PA nanofiber were examined under fluorescent microscopy. The 75% RTL PA nanofiber was chosen for this study because this ligand density resulted in the greatest binding to the site of injury without impacting MAP. After liver injury and injection of the TF-targeted nanofiber, no fluorescent signal was detected in the uninjured liver, kidney, or spleen (FIG. 8, Panels A-C). A very small amount of fluorescence was noted in the lung tissue (FIG. 8, Panel D).

Example 10

Protected Group Thrombin Therapeutic

Peptide amphiphiles containing the protected group thrombin are synthesized and characterized similarly to the Examples 1-9. Further, the ability of recombinant Factor Xa to cleave Factor X from the thrombin molecule is assessed using a commercially available fluorometric thrombin activity assay. Experiments are conducted to identify PA nanofibers containing a thrombin molecule protected by Factor X that becomes active once Factor X is cleaved by Factor Xa.

REFERENCES

The following references, some of which are cited above by number, are incorporated herein by reference in their entireties 1. Hoyt, D. B.; Bulger, E. M.; Knudson, M. M.; Morris, J.; Ierardi, R.; Sugerman, H. J.; Shackford, S. R.; Landercasper, J.; Winchell, R. J.; Jurkovich, G.; Death in the Operating Room: an Analysis of a Multi-Center Experience. *J. Trauma* 1994, 37, 426-432.
2. Eastridge, B. J.; Hardin, M.; Cantrell, J.; Oetjen-Gerdes, L.; Zubko, T.; Mallak, C.; Wade, C. E.; Simmons, J.; Mace, J.; Mabry, R.; Bolenbaucher, R.; Blackbourne, L. H. Died of Wounds on the Battlefield: Causation and Implications for Improving Combat Casualty Care. *J. Trauma* 2011, 71, S4-S8.
3. Morrison, J. J.; Rasmussen, T. E. Noncompressible Torso Hemorrhage: a Review with Contemporary Definitions and Management Strategies. *Surg. Clin. North Am.* 2012, 92, 843-58, vii.
4. Stannard, A.; Morrison, J. J.; Scott, D. J.; Ivatury, R. A.; Ross, J. D.; Rasmussen, T. E. The Epidemiology of Noncompressible Torso Hemorrhage in the Wars in Iraq and Afghanistan. *J. Trauma Acute. Care Surg.* 2013, 74, 830-834.
5. Ketchum, L.; Hess, J. R.; Hiippala, S. Indications for Early Fresh Frozen Plasma, Cryoprecipitate, and Platelet Transfusion in Trauma. *J Trauma* 2006, 60, S51-58.
6. Hauser, C. J.; Boffard, K.; Dutton, R.; Bernard, G. R.; Croce, M. A.; Holcomb, J. B.; Leppaniemi, A.; Parr, M.; Vincent, J. L.; Tortella, B. J.; Dimsits, J.; Bouillon, B.; Group, C. S. Results of the CONTROL Trial: Efficacy and Safety of Recombinant Activated Factor VII in the Management of Refractory Traumatic Hemorrhage. *J Trauma* 2010, 69, 489-500.

7. Dutton, R. P.; Parr, M.; Tortella, B. J.; Champion, H. R.; Bernard, G. R.; Boffard, K.; Bouillon, B.; Croce, M. A.; Dimsits, J.; Holcomb, J. B.; Leppaniemi, A.; Vincent, J. L.; Hauser, C. J.; Group, C. S. Recombinant Activated Factor VII Safety in Trauma Patients: Results from the CONTROL Trial. *J Trauma* 2011, 71, 12-19.

8. Neufeld, E. J.; Negrier, C.; Arkhammar, P.; Benchikh el Fegoun, S.; Simonsen, M. D.; Rosholm, A.; Seremetis, S. Safety Update on the Use of Recombinant Activated Factor VII in Approved Indications. *Blood Rev* 2015, 29 Suppl 1, S34-S41.

9. Colman, R. W. *Hemostasis and Thrombosis: Basic Principles and Clinical Practice. Chapter 5: Tissue Factor Structure and Function.* Authors: James H. Morrissey, Nicola J. Mutch. Pages 91-101. 5th ed.; Lippincott Williams & Wilkins: Philadelphia, 2006.

10. Hartgerink, J. D.; Beniash, E.; Stupp, S. I. Self-Assembly and Mineralization of Peptide-Amphiphile Nanofibers. *Science* 2001, 294, 1684-1688.

11. Hartgerink, J. D.; Beniash, E.; Stupp, S. I. Peptide-Amphiphile Nanofibers: a Versatile Scaffold for the Preparation of Self-assembling Materials. *Proc Natl Acad Sci USA* 2002, 99, 5133-5138.

12. Webber, M. J.; Berns, E. J.; Stupp, S. I. Supramolecular Nanofibers of Peptide Amphiphiles for Medicine. *Isr J Chem* 2013, 53, 530-554.

13. Rubert Perez, C. M.; Stephanopoulos, N.; Sur, S.; Lee, S. S.; Newcomb, C.; Stupp, S. I. The Powerful Functions of Peptide-based Bioactive Matrices for Regenerative Medicine. *Ann Biomed Eng* 2015, 43, 501-514.

14. Moyer, T. J.; Kassam, H. A.; Bahnson, E. S.; Morgan, C. E.; Tantakitti, F.; Chew, T. L.; Kibbe, M. R.; Stupp, S. I. Shape-Dependent Targeting of Injured Blood Vessels by Peptide Amphiphile Supramolecular Nanostructures. *Small* 2015, 11, 2750-2755.

15. Toft, D. J.; Moyer, T. J.; Standley, S. M.; Ruff, Y.; Ugolkov, A.; Stupp, S. I.; Cryns, V. L. Coassembled Cytotoxic and Pegylated Peptide Amphiphiles Form Filamentous Nanostructures with Potent Antitumor Activity in Models of Breast Cancer. *ACS Nano* 2012, 6, 7956-7965.

16. Cui, H.; Webber, M. J.; Stupp, S. I. Self-Assembly of Peptide Amphiphiles: from Molecules to Nanostructures to Biomaterials. *Biopolymers* 2010, 94, 1-18.

17. Sridhara, S.; Clarke, B. J.; Blajchman, M. A. Arginine-79 in the First Epidermal Growth Factor Domain of Factor VII is Essential for the Interaction with Tissue Factor. *Blood Coagul Fibrinolysis* 1993, 4, 505-508.

18. Dickinson, C. D.; Kelly, C. R.; Ruf, W. Identification of Surface Residues Mediating Tissue Factor Binding and Catalytic Function of the Serine Protease Factor VIIa. *Proc Natl Acad Sci USA* 1996, 93, 14379-14384.

19. Banner, D. W.; D'Arcy, A.; Chène, C.; Winkler, F. K.; Guha, A.; Konigsberg, W. H.; Nemerson, Y.; Kirchhofer, D. The Crystal Structure of the Complex of Blood Coagulation Factor VIIa with Soluble Tissue Factor. *Nature* 1996, 380, 41-46.

20. Potter, D. R.; Baimukanova, G.; Keating, S. M.; Deng, X.; Chu, J. A.; Gibb, S. L.; Peng, Z.; Muench, M. O.; Fomin, M. E.; Spinella, P. C.; Kozar, R.; Pati, S. Fresh frozen plasma and spray-dried plasma mitigate pulmonary vascular permeability and inflammation in hemorrhagic shock. *J Trauma Acute Care Surg* 2015, 78, S7-S17.

21. Bertram, J. P.; Williams, C. A.; Robinson, R.; Segal, S. S.; Flynn, N. T.; Lavik, E. B. Intravenous Hemostat: Nanotechnology to Halt Bleeding. *Sci. Transl. Med.* 2009, 1, 11ra22.

22. Shoffstall, A. J.; Atkins, K. T.; Groynom, R. E.; Varley, M. E.; Everhart, L. M.; Lashof-Sullivan, M. M.; Martyn-Dow, B.; Butler, R. S.; Ustin, J. S.; Lavik, E. B. Intravenous Hemostatic Nanoparticles Increase Survival Following Blunt Trauma Injury. *Biomacromolecules.* 2012, 13, 3850-3857.

23. Lashof-Sullivan, M. M.; Shoffstall, E.; Atkins, K. T.; Keane, N.; Bir, C.; VandeVord, P.; Lavik, E. B. Intravenously Administered Nanoparticles Increase Survival Following Blast Trauma. *Proc Natl Acad Sci USA* 2014, 111, 10293-10298.

24. Chan, L. W.; Wang, X.; Wei, H.; Pozzo, L. D.; White, N. J.; Pun, S. H. A Synthetic Fibrin Cross-linking Polymer for Modulating Clot Properties and Inducing Hemostasis. *Sci Transl Med* 2015, 7, 277ra29.

25. Shoffstall, A. J.; Everhart, L. M.; Varley, M. E.; Soehnlen, E. S.; Shick, A. M.; Ustin, J. S.; Lavik, E. B. Tuning Ligand Density on Intravenous Hemostatic Nanoparticles Dramatically Increases Survival Following Blunt Trauma. *Biomacromolecules.* 2013, 14, 2790-2797.

26. Bahnson, E. S.; Kassam, H. A.; Moyer, T. J.; Jiang, W.; Morgan, C. E.; Vercammen, J. M.; Jiang, Q.; Flynn, M. E.; Stupp, S. I.; Kibbe, M. R. Targeted Nitric Oxide Delivery by Supramolecular Nanofibers for the Prevention of Restenosis after Arterial Injury. *Antioxid Redox Signal* 2015. (in press)

27. Morgan, C. E.; Prakash, V. S.; Vercammen, J. M.; Pritts, T.; Kibbe, M. R. Development and Validation of 4 Different Rat Models of Uncontrolled Hemorrhage. *JAMA Surg* 2015, 150, 316-324.

The invention claimed is:

1. A nanofiber comprising a self-assembled complex of peptide amphiphiles comprising
   (a) tissue factor (TF)-targeted peptide amphiphiles that comprise a hydrophobic non-peptide tail, a structured peptide segment, a charged peptide segment, and a terminal TF-targeted peptide;
   (b) therapeutic peptide amphiphiles that comprise a hydrophobic non-peptide tail, a structured peptide segment, a charged peptide segment, and a terminal therapeutic moiety; and
   (c) filler peptide amphiphiles that comprise a hydrophobic non-peptide tail, a structured peptide segment, and a charged peptide segment, but do not comprise a terminal bioactive moiety.

2. The nanofiber of claim 1, wherein the hydrophobic non-peptide tails of the TF-targeted peptide amphiphiles, the therapeutic peptide amphiphiles, and the filler peptide amphiphiles comprise an 8-24 carbon alkyl chain ($C_{8-24}$).

3. The nanofiber of claim 1, wherein the TF-targeted peptide amphiphiles, the therapeutic peptide amphiphiles, and/or the filler peptide amphiphiles comprises a K residue, and wherein the hydrophobic non-peptide tail is attached to the sidechain of the K residue.

4. The nanofiber of claim 1, wherein the structured peptide segment of the TF-targeted peptide amphiphiles, the therapeutic peptide amphiphiles, and the filler peptide amphiphiles comprises VVAA (SEQ ID NO: 4) or any suitable combination of V and/or A residues.

5. The nanofiber of claim 1, wherein the structured peptide segment of the TF-targeted peptide amphiphiles, the therapeutic peptide amphiphiles, and the filler peptide amphiphiles has propensity to form β-sheet-like structures with adjacent structured peptide segments.

6. The nanofiber of claim 1, wherein the charged peptide segment of the TF-targeted peptide amphiphiles, the therapeutic peptide amphiphiles, and the filler peptide amphiphiles comprises an acidic, basic, or zwitterionic peptide segment.

7. The nanofiber of claim 1, wherein the charged peptide segment of the TF-targeted peptide amphiphiles, the therapeutic peptide amphiphiles, and the filler peptide amphiphiles comprises EE or KK.

8. The nanofiber of claim 1, wherein the TF-targeted peptide amphiphiles, the therapeutic peptide amphiphiles, and the filler peptide amphiphiles comprise KKAAVV(K)-$C_{8-24}$ (SEQ ID NO: 5).

9. The nanofiber of claim 1, wherein the charged peptide segment is the terminal segment of the filler peptide amphiphile.

10. The nanofiber of one of claim 1, wherein the terminal therapeutic moiety of the therapeutic peptide amphiphiles is a procoagulant agent.

11. The nanofiber of claim 10, wherein the procoagulant moiety is thrombin.

12. The nanofiber of claim 10, wherein the procoagulant moiety is shielded to inhibit the bioactivity of the procoagulant moiety until a shielding moiety is removed.

13. The nanofiber of claim 12, wherein the procoagulant moiety is thrombin and the shielding moiety is Factor X.

14. A kit comprising the nanofiber of one of claim 1, and one or more additional components for delivering the nanofiber, storing the nanofiber, and/or for the treatment of hemorrhage and/or an acute injury.

15. A method of treating or preventing hemorrhage in a subject comprising administering a nanofiber of claim 10 to a subject suffering from an acute injury.

16. The method of claim 15, wherein the nanofiber is pharmaceutically formulated.

17. The method of claim 15, wherein the nanofiber is administered by injection to a hemorrhagic or potentially-hemorrhagic site.

18. The method of claim 15, wherein the nanofiber is co-administered with one or more additional treatments or therapies for hemorrhage and/or the acute injury.

* * * * *